(12) United States Patent
Kley et al.

(10) Patent No.: US 9,018,215 B2
(45) Date of Patent: Apr. 28, 2015

(54) HETEROAROMATIC COMPOUNDS, MEDICAMENTS CONTAINING SAID COMPOUNDS, USE THEREOF AND PROCESSES FOR THE PREPARATION THEREOF

(71) Applicants: Joerg Kley, Mittelbiberach (DE); Armin Heckel, Biberach an der Riss (DE)

(72) Inventors: Joerg Kley, Mittelbiberach (DE); Armin Heckel, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/262,903

(22) Filed: Apr. 28, 2014

(65) Prior Publication Data
US 2014/0323447 A1   Oct. 30, 2014

(30) Foreign Application Priority Data

Apr. 30, 2013   (EP) .................................... 13165963

(51) Int. Cl.
| | | |
|---|---|---|
| *C07D 401/14* | (2006.01) | |
| *C07D 409/14* | (2006.01) | |
| *C07D 417/14* | (2006.01) | |
| *A61K 31/497* | (2006.01) | |
| *A61K 45/06* | (2006.01) | |
| *C07D 471/04* | (2006.01) | |
| *A61K 31/517* | (2006.01) | |

(52) U.S. Cl.
CPC ............ *C07D 401/14* (2013.01); *A61K 31/497* (2013.01); *C07D 471/04* (2013.01); *C07D 417/14* (2013.01); *C07D 409/14* (2013.01); *A61K 45/06* (2013.01); *A61K 31/517* (2013.01)

(58) Field of Classification Search
CPC .. C07D 401/14; C07D 409/14; C07D 417/14; A61K 31/497; A61K 45/06
USPC ...................................... 514/255.05; 544/405
See application file for complete search history.

(56) References Cited

FOREIGN PATENT DOCUMENTS

| | | | |
|---|---|---|---|
| EP | 2012-169577 | * | 5/2012 |
| EP | 2465852 A1 | | 6/2012 |
| WO | 2008135557 A1 | | 11/2008 |
| WO | 2013092674 A1 | | 6/2013 |
| WO | 2013174757 | | 11/2013 |

OTHER PUBLICATIONS

Hirsh, et al, J. Med. Chem, "Design, Synthesis, and Structure-Activity Relationshiops of Novel 2-Substituted Pyrazinoylguanidine Epithlial Sodium Channel Blockers: Drugs for Cystic Fibrosis and Chronic Bronchitis", 2006, p. 4098-4115.

* cited by examiner

*Primary Examiner* — Erich A Leeser
(74) *Attorney, Agent, or Firm* — Michael P. Morris; Edward S. Lazer

(57) ABSTRACT

The present invention relates to compounds of general formula (I)

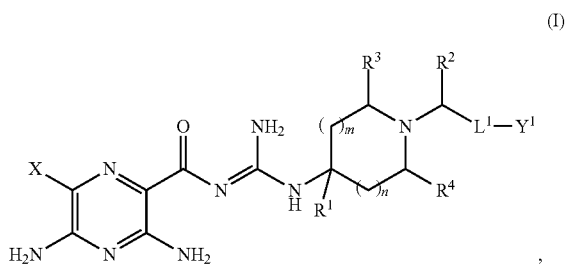

and the tautomers and the salts thereof, particularly the pharmaceutically acceptable salts thereof with inorganic or organic acids and bases, which have valuable pharmacological properties, particularly an inhibitory effect on epithelial sodium channels and the use thereof for the treatment of diseases, particularly diseases of the lungs and airways.

12 Claims, No Drawings

HETEROAROMATIC COMPOUNDS, MEDICAMENTS CONTAINING SAID COMPOUNDS, USE THEREOF AND PROCESSES FOR THE PREPARATION THEREOF

1. FIELD OF THE INVENTION

The present invention relates to compounds of general formula (I)

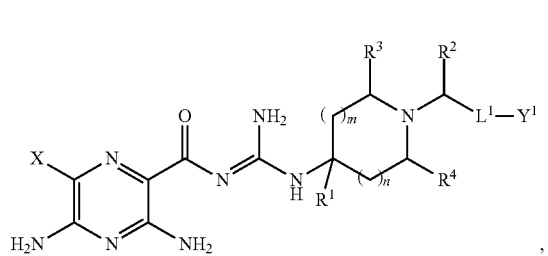

(I)

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

2. BACKGROUND OF THE INVENTION

Amiloride type compounds are known from the prior art as active substances for example for the treatment of diseases of the lungs and airways (*J. Med. Chem.* 49 (2006) 4098-4115). WO 08135557 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways.

3. DETAILED DESCRIPTION OF THE INVENTION

It has surprisingly been found that the problem mentioned above is solved by compounds of formula (I) of the present invention.

The present invention therefore relates to a compound of formula (I),

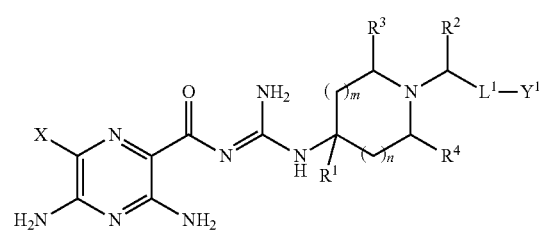

(I)

wherein
$R^1$ denotes H or methyl,
$R^2$ is selected from a group consisting of
  H, $C_{1-4}$-alkyl-, $C_{1-4}$-alkyl-O—CO—, $C_{1-4}$-alkyl-O—CO—$C_{1-4}$-alkyl-, $C_{1-4}$-alkyl-O—$C_{1-4}$-alkyl-, HO—CO— and HO—CO—$C_{1-4}$-alkyl-,
$R^3$ denotes H or methyl,
$R^4$ denotes H or methyl, or
$R^3$ and $R^4$ together form an ethylene bridge
m, n independently from each other with the proviso that (m+n)<4, denote 0, 1 or 2,
X denotes halogen,
$L^1$ denotes a bond or is selected from a group consisting of
  —$CH_2$—, —$CH_2$—$CH_2$—, —$CH_2O$—, —CO—, —S—, —SO—, —$SO_2$—, —S—$CH_2$—, SO—$CH_2$— and —$SO_2$—$CH_2$—
$Y^1$ denotes a C-linked five- or six membered heteroaromatic moiety or a C-linked 8-10-membered heteroaromatic moiety, optionally substituted by $R^5$, $R^6$, $R^7$, and $R^8$, wherein
$R^7$ and $R^8$ independently from each other are selected from a group consisting of
  H, halogen, CN, $C_{1-4}$-alkyl-, optionally substituted by one or more F atoms, HC≡C—, OH, $C_{1-4}$-alkyl-O— and HO—$CH_2$—,
$R^5$ is selected from a group consisting of
  H, halogen, =O, CN, $N_3$, $C_{1-4}$-alkyl-, optionally substituted by one or more F atoms,
  HC≡C—, OH, $C_{1-4}$-alkyl-O—, HO—$CH_2$—,
  $H_2C$=CH—$CH_2$—O—, HC≡C—$CH_2$—, HC≡C—$CH_2$—O—, —$NR^{5.1}R^{5.2}$,
  $H_2N$—C(NH)—, $H_2N$—C(NH)NH—, $H_2N$—C(NH)NH—$CH_2$—, —COOH, $C_{1-4}$-alkyl-OCO—, $C_{1-4}$-alkyl-COOH, —$C_{1-4}$-alkyl-COO—$C_{1-4}$-alkyl-, —$OCH_2$—COOH, —$OCH_2$—COO—$C_{1-4}$-alkyl, and —$B(OH)_2$,
wherein,
  $R^{5.1}$ denotes H, $C_{1-4}$-alkyl-, $C_{1-4}$-alkyl-CO— or $C_{1-4}$-alkyl-$SO_2$—,
  $R^{5.2}$ denotes H or $C_{1-4}$-alkyl-,
or
  $R^{5.1}$ and $R^{5.2}$ together with the nitrogen atom they are attached to form an optionally substituted 4-7-membered heterocycle containing at least one N-atom,
$R^6$ is selected from a group consisting of
  H, halogen, =O, CN, $N_3$, $C_{1-4}$-alkyl-, optionally substituted by one or more F atoms,
  HC≡C—, OH, $C_{1-4}$-alkyl-O—, HO—$CH_2$—,
  $H_2C$=CH—$CH_2$—O—, HC≡C—$CH_2$—, HC≡C—$CH_2$—O—, —$NR^{6.1}R^{6.2}$,
  $H_2N$—C(NH)—, $H_2N$—C(NH)NH—, $H_2N$—C(NH)NH—$CH_2$—, —COOH, $C_{1-4}$-alkyl-OCO—, —$C_{1-4}$-alkyl-COOH, —$C_{1-4}$-alkyl-COO—$C_{1-4}$-alkyl, —$OCH_2$—COOH, —$OCH_2$—COO—$C_{1-4}$-alkyl, and —$B(OH)_2$,
is wherein,
  $R^{6.1}$ denotes H, $C_{1-4}$-alkyl-, $C_{1-4}$-alkyl-CO— or $C_{1-4}$-alkyl-$SO_2$—,
  $R^{6.2}$ denotes H or $C_{1-4}$-alkyl-,
or
  $R^{6.1}$ and $R^{6.2}$ together with the nitrogen atom they are attached to form an optionally substituted 4-7-membered heterocycle containing at least one N-atom,
or
$R^6$ denotes -$L^2$-$Y^2$-$L^3$-$R^{6.5}$ wherein,
L² denotes a bond or is selected from a group consisting of —CH₂—, —CH₂—CH₂—, and —CH₂—CO—,
or, with the proviso that L² is attached to a carbon atom of Y¹, is selected from a group consisting of —O—, —CH₂—O—, —O—CH₂—, —CO—, —CO—CH₂—, —S—, —SO—, —SO₂— and —O—CO—
Y² denotes a bond or
is selected from a group consisting of Y²·¹, —CO—, NR¹¹—CO—, —CO—NR¹¹—, —Y²·¹—CONR¹¹—, —Y²·¹—CO— and —NR¹¹—CO—Y²·¹—, with the proviso that carbonyl moieties are not directly attached to nitrogen atoms of unsaturated heterocycles and are not directly attached to another carbonyl moiety,
wherein
R¹¹ denotes -L⁴-R⁹
Y²·¹ denotes a cyclic linker selected from either a phenylene group optionally substituted by -L⁵R¹⁰, or
an optionally substituted heteroaromatic or heterocyclic moiety each containing at least one nitrogen atom,
L³, L⁴, L⁵ independently from each other denote a bond or a linear chain of formula (m)

—(CH₂)ᵢ—[O—(CH₂)g1]p1—[O—(CH₂)g2]p2—   (m)

wherein
i denotes 0, 1, 2 or 3
g1, g2 independently from each other denote 2 or 3,
p1, p2 independently from each other denote 0, 1, 2 or 3, with the provisio that the linear chain is consisting of 1 to 12 moieties selected from a group consisting of —CH₂—, and —O—.
R⁶·⁵, R⁹, R¹⁰ independently from each other are selected from a group consisting of H, halogen, CN, C₁₋₄-alkyl, HC≡C—, OH, C₁₋₄-alkyl-O—, HO—CH₂—, H₂C=CH—CH₂—O—, HC≡C—CH₂—O—, B(OH)₂, BF₃⁻, —S(O)₂OH, —C(CH₂OH)₃, —CH(CH₂OH)₂, and —CH(OH)CH₂OH
or
independently from each other denote a five- or six membered heteroaromatic or heterocyclic moiety, optionally substituted by one or two substituents independently selected from
halogen, CN, C₁₋₄-alkyl-, optionally substituted by one or more F atoms, HC≡C—, OH, C₁₋₄-alkyl-O— and HO—CH₂—,
and tautomers and optionally hydrates, solvates, polymorphs, pharmaceutically acceptable prodrugs or the pharmaceutically acceptable acid addition salts thereof, preferably, the pharmaceutically acceptable acid addition salts thereof.

Preferred compounds of formula (I) are those wherein
m, n independently from each other with the proviso that 0<(m+n)<4, denote 0, 1 or 2,
X denotes Cl or Br, and
L¹ denotes a bond or is selected from a group consisting of —CH₂— and —CH₂—CH₂—,
Y¹ is selected from a group consisting of a linker of formula (a1) to (k1)

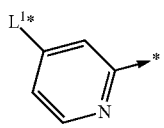
(a1)

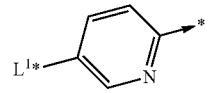
(b1)

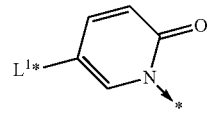
(c1)

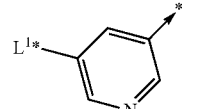
(d1)

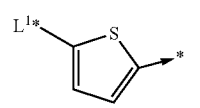
(e1)

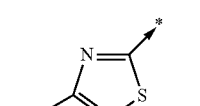
(f1)

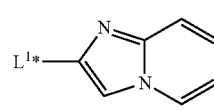
(g1)

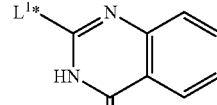
(h1)

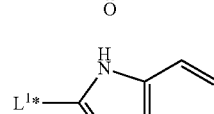
(i1)

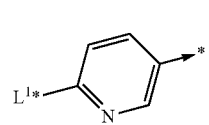
(k1)

✳ denotes the attachment point to a substituent of Y¹
L¹* denotes the attachment point to L¹

Particularly preferred are compounds of formula (I), wherein
R¹, R², R³ and R⁴ denote hydrogen,
m, n denote 1, and
L¹ denotes a bond.

Also particularly preferred are compounds of formula (I), wherein
R⁵ denotes hydrogen or is selected from a group consisting of halogen, =O and methyl,
R⁶ denotes hydrogen or is selected from a group consisting of C₁₋₄-alkyl-OCO—, HC≡C—, halogen, HC≡C—CH₂— and —COOH, or
R⁶ denotes -L²-Y²-L³-R⁶·⁵ wherein,
L² denotes a bond or is selected from a group consisting of
—CH₂— and —CH₂—CH₂—,
Y² denotes a bond or
is selected from a group consisting of
$Y^{2.1}$, —CO—, —CO—NR¹¹—,
with the proviso that carbonyl moieties are not directly attached to nitrogen atoms of unsaturated heterocycles and are not directly attached to another carbonyl moiety,
wherein
$R^{11}$ denotes -$L^4$-$R^9$,
$Y^{2.1}$ denotes a pyridyl or triazolyl moiety,
$L^3$, $L^4$ independently from each other denote a bond or a linear chain of formula (m)

$$-(CH_2)_i-[O-(CH_2)_{g1}]_{p1}-[O-(CH_2)_{g2}]_{p2}- \quad (m)$$

wherein
i denotes 0, 1, 2 or 3,
g1, g2 independently from each other denote 2,
p1, p2 independently from each other denote 0, 1 or 2,
$R^{6.5}$, $R^9$ independently from each other denote H or OH,
or
$R^{6.5}$ denotes pyridyl,
$R^7$, $R^8$ denote hydrogen.

Also particularly preferred are compounds of formula (I), wherein
$R^1$ denotes H,
$R^2$ denotes H,
X denotes Cl or Br,
$L^1$ denotes a bond or is selected from a group consisting of —CH₂—, —CH₂—CH₂—, —CH₂O—, and —CO—,
$Y^1$ denotes a moiety selected from a group consisting of a linker of formula (a1) to (z1)

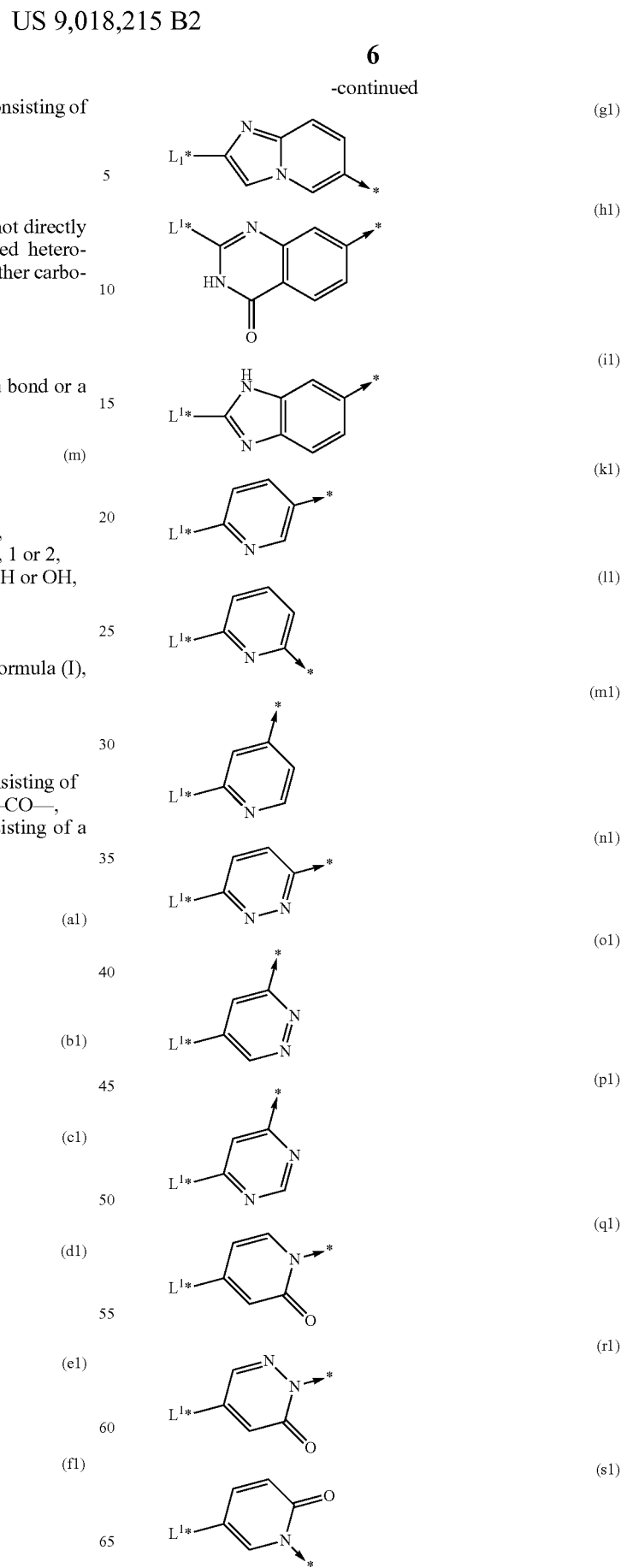

-continued

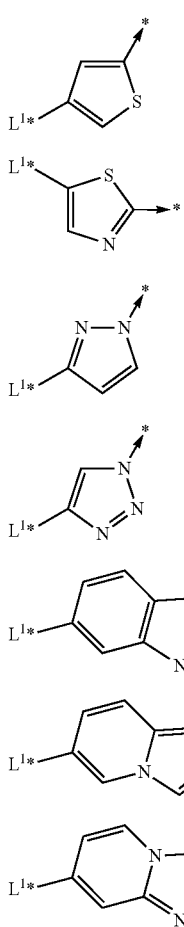

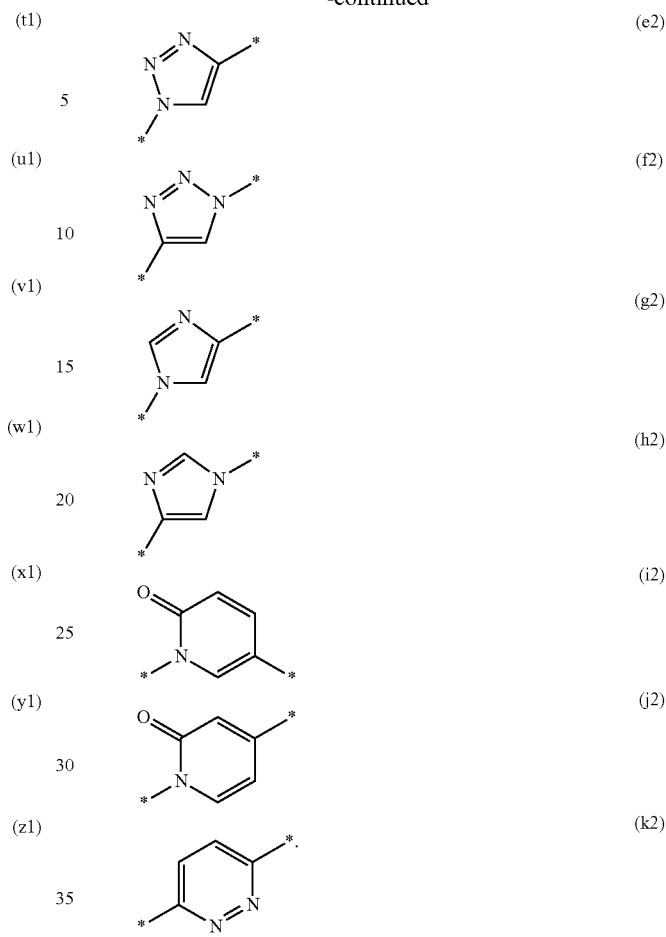

⟋ denotes the attachment point to a substituent of Y¹,
L¹* denotes the attachment point to L¹,
each optionally substituted by R⁵ or R⁶,
Y$^{2.1}$ is selected from a group consisting of a linker of formula (a2) to (k2)

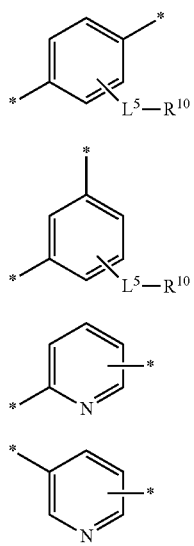

Also particularly preferred are compounds of formula (I), wherein
a compound of formula (I) according to anyone of claim 1, 2 or 5 is characterized in that
R³, R⁴ denote H,
m, n independently from each other with the proviso that 0<(m+n)<4, denote 0, 1 or 2,
X denotes Cl or Br,
L¹ denotes a bond or is selected from a group consisting of —CH₂—, and —CH₂—CH₂—,
R$^{6.5}$, R⁹, R¹⁰ independently from each other are selected from a group consisting of H, HC≡C—, OH and 2-pyridyl.

Also particularly preferred are compounds of formula (I), wherein
R⁵ is selected from a group consisting of
  H, halogen and C$_{1-4}$-alkyl-, optionally substituted by one or more F atoms,
R⁶ denotes —COOH, and
Y¹ is selected from among (a1), (b1), (d1), (e1) and (g1).

Also particularly preferred are compounds of formula (I), wherein
R⁵ is selected from a group consisting of
  H, halogen, C$_{1-4}$-alkyl-(optionally substituted by one or more F atoms),
R⁶ denotes C$_{1-4}$-alkyl-OCO—, and
Y¹ is selected from among (a1), (b1), (d1), (e1) and (g1).

Also particularly preferred are compounds of formula (I), wherein
$R^6$ denotes -$L^2$-$Y^2$-$L^3$-$R^{6.5}$
wherein,
$L^2$ denotes a bond or is selected from a group consisting of —$CH_2$—, and —$CH_2$—$CH_2$—,
or, with the proviso that $L^2$ is attached to a carbon atom of $Y^1$, is selected from a group consisting of —O—, —$CH_2$—O—, and —O—$CH_2$—,
$Y^2$ denotes —CO—$NR^{11}$— or —$Y^{2.1}$—$CONR^{11}$—,
with the proviso that carbonyl moieties are not directly attached to nitrogen atoms of unsaturated heterocycles and are not directly attached to another carbonyl moiety,
$L^3$, $L^4$, $L^5$ independently from each other denote a bond or a linear chain of formula (m)

$$—(CH_2)_i—[O—(CH_2)_{g1}]_{p1}—[O—(CH_2)_{g2}]_{p2}— \quad (m)$$

wherein
I denotes 0, 1, 2 or 3,
g1, g2 independently from each other denote 2 or 3,
p1, p2 independently from each other denote 0, 1, 2 or 3,
with the provisio that the linear chain is consisting of 1 to 12 moieties selected from a group consisting of —$CH_2$—, and —O—,
and with the proviso that p1+p2<4.
Also particularly preferred are compounds of formula (I), wherein
$R^6$ denotes -$L^2$-$Y^2$-$L^3$-$R^{6.5}$
wherein,
at least one out of $L^3$, $L^4$, and $L^5$ denotes a linear chain of formula (m)

$$—(CH_2)_i—[O—(CH_2)_{g1}]_{p1}—[O—(CH_2)_{g2}]_{p2}— \quad (m)$$

wherein
i denotes 0, 1, 2 or 3
g1, g2 independently from each other denote 2 or 3,
p1, p2 independently from each other denote 0, 1, 2 or 3,
with the provisio that the linear chain consists of 6 to 12 moieties selected from a group consisting of —$CH_2$—, and —O—
and with the proviso that p1+p2>1.

A further embodiment of the current invention are compounds of formula (I) or a pharmaceutically acceptable salt thereof for use as a medicament.

A further embodiment of the current invention are compounds of formula (I), or a pharmaceutically acceptable salt thereof for use in the treatment of a disease selected from among respiratory diseases or complaints and allergic diseases of the airways.

Preferred are compounds of formula (I) or a pharmaceutically acceptable salt thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins.

A further embodiment of the current invention is a pharmaceutical composition comprising at least one compound according to the invention or a pharmaceutically acceptable salt thereof and a pharmaceutically acceptable carrier.

A further embodiment of the current invention is medicament combinations which contain, besides one or more compounds according to the invention and, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

4. TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general, in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal bond indicates the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

If a compound of the present invention is depicted in the form of a chemical name and also as a formula, in case of any discrepancy the formula shall prevail. An asterisk may be used in sub-formulas to indicate the bond which is connected to the core molecule as defined.

For example, the term "3-carboxypropyl-group" represents the following substituent:

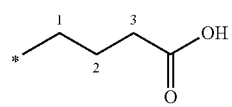

wherein the carboxy group is attached to the third carbon atom of the propyl group. The terms "1-methylpropyl-", "2,2-dimethylpropyl-" or "cyclopropylmethyl-" group represent the following groups:

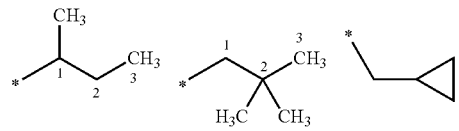

The asterisk may be used in sub-formulas to indicate the bond which is connected to the core molecule as defined.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods.

Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

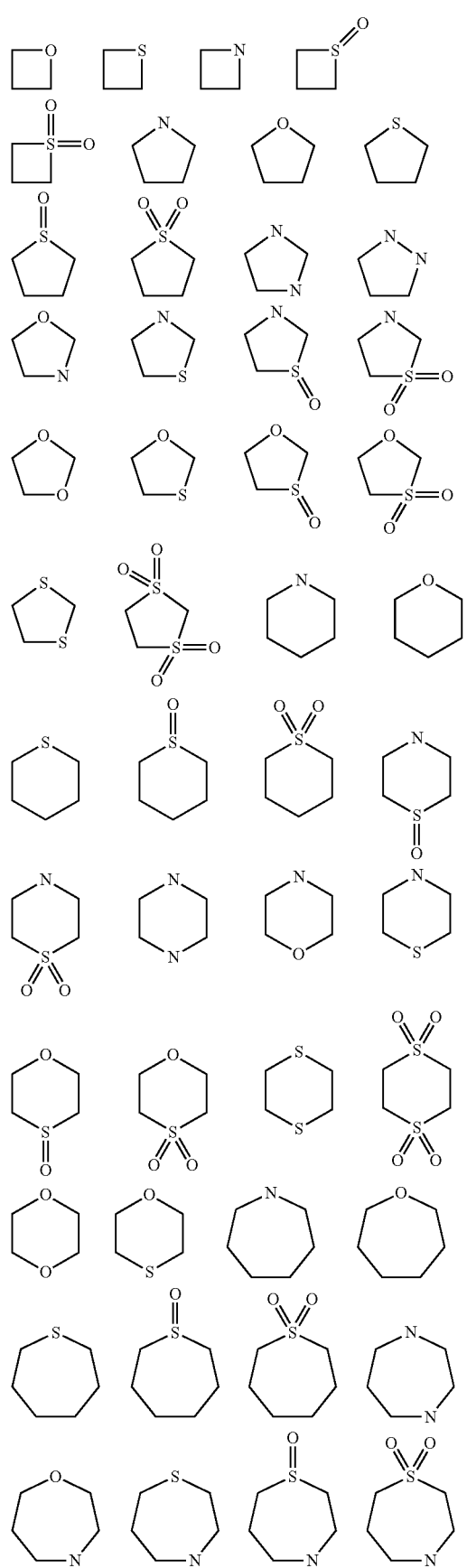
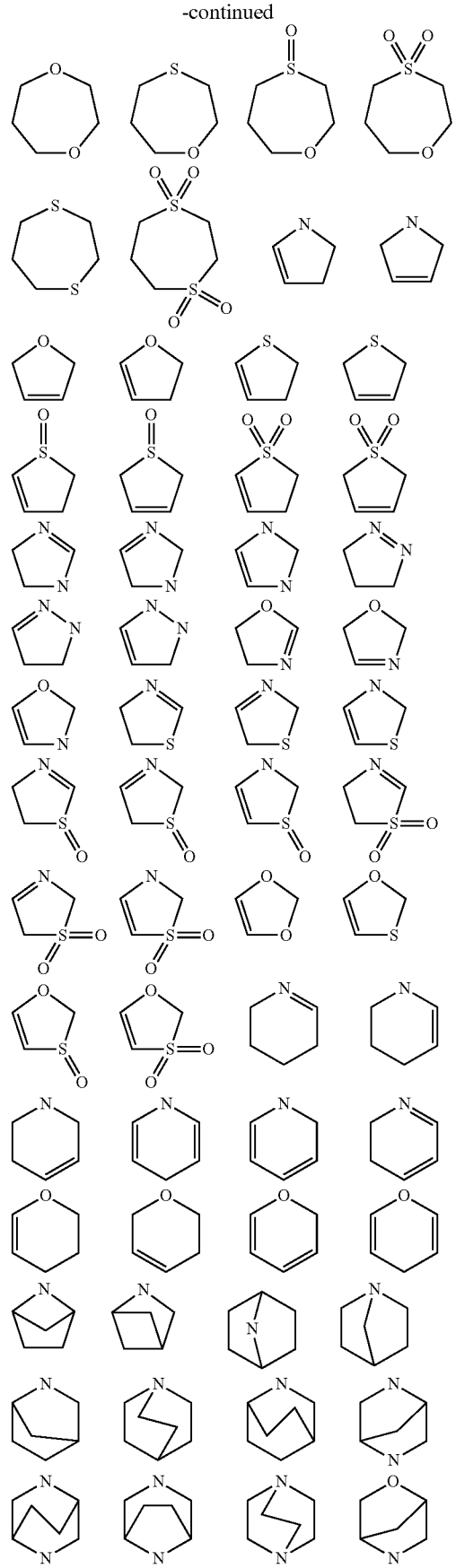

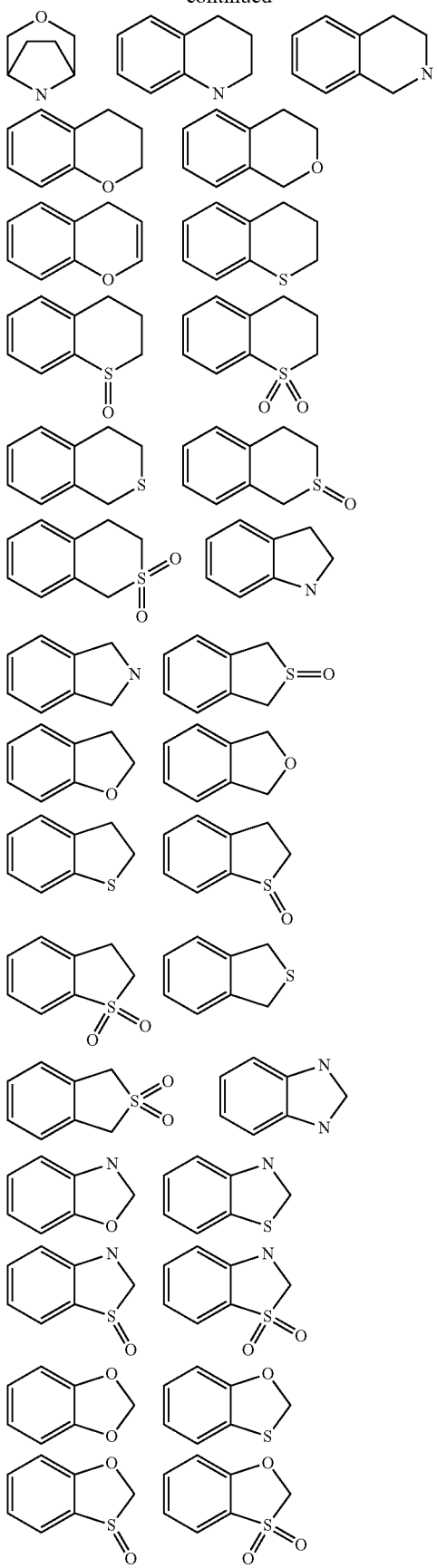
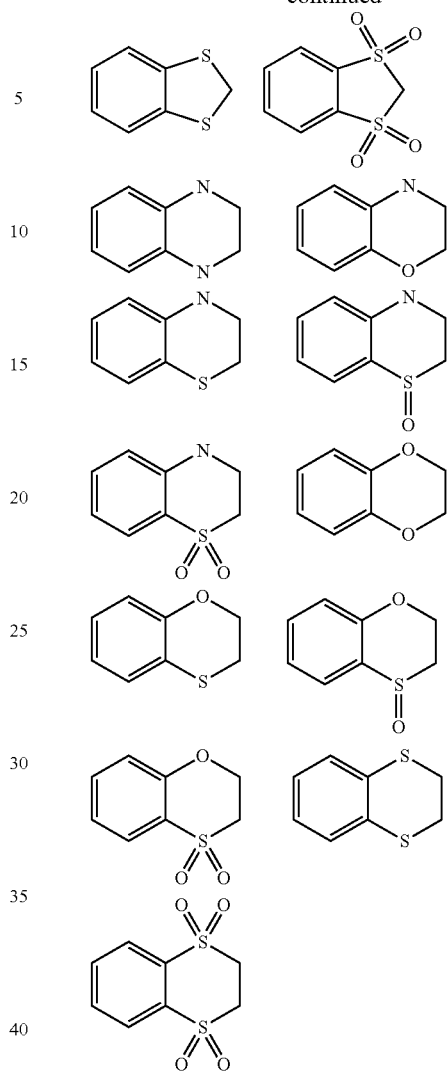

The term heteroaromatic means heteroaryl, monocyclic $C_{5-6}$-heteroaryl, or bicyclic $C_{8-14}$-heteroaryl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

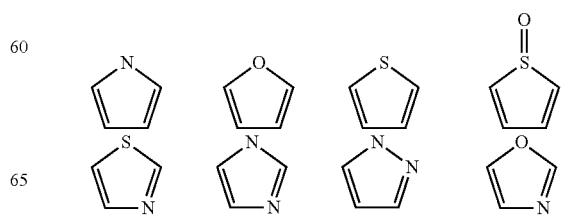

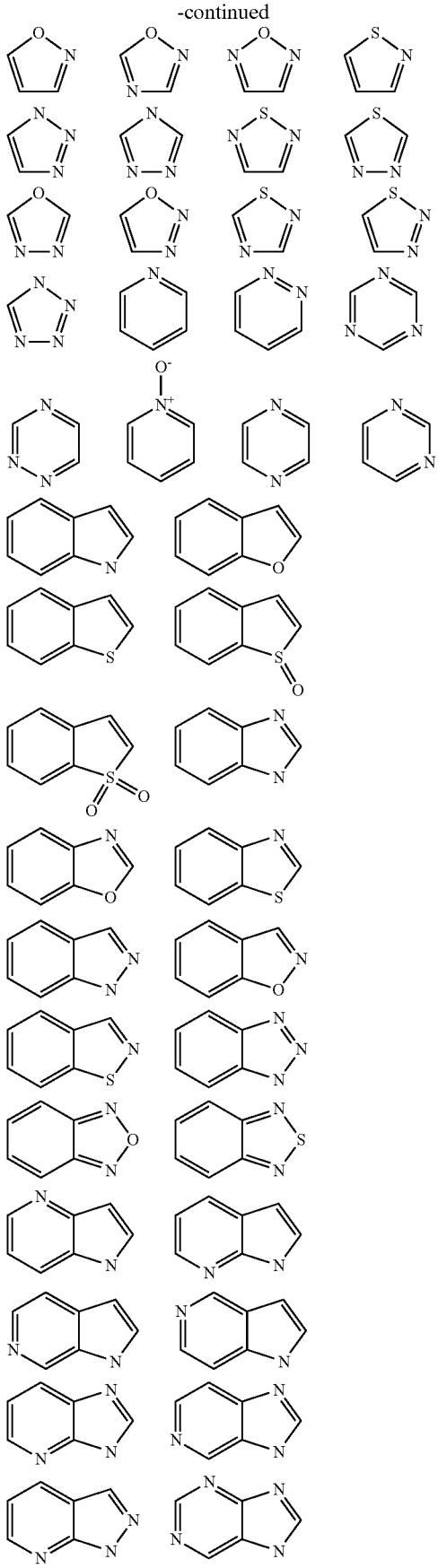

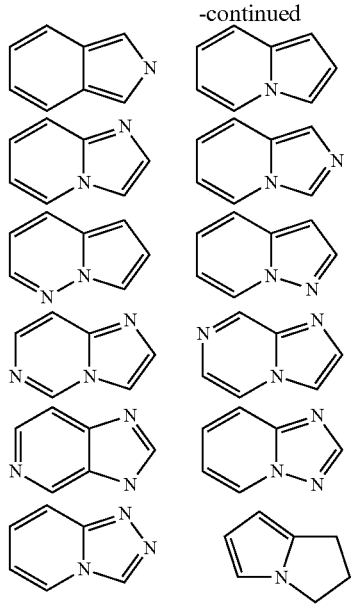

The term "monocyclic $C_{5-6}$-heteroaryl" means a monocyclic-ring system containing one or more heteroatoms selected from N, O or $S(O)_r$, wherein r=0, 1 or 2, consisting of 5 or 6 ring atoms wherein at least one of the heteroatoms is part of aromatic ring. The term "monocyclic $C_{5-6}$-heteroaryl" is intended to include all the possible isomeric forms.

Examples of bicyclic heteroaryl rings include pyrrolizine, indole, indolizine, isoindole, indazole, purine, quinoline, isoquinoline, benzimidazole, benzofuran, benzopyrane, benzothiazole, benzo) isothiazole, pyridopyrimidine, pteridine, pyrimidopyrimidine.

The term "monocyclic $C_{5-7}$-heterocyclyl" means a saturated or unsaturated non-aromatic monocyclic-ring system containing one or more heteroatoms selected from N, O or $S(O)_r$, wherein r=0, 1 or 2, consisting of 5 to 7 ring atoms. The term "monocyclic $C_{5-7}$-heterocyclyl" is intended to include all the possible isomeric forms.

Thus, the term "monocyclic $C_{5-7}$-heterocyclyl" includes the following exemplary structures which are not depicted as radicals as each form may be attached through a covalent bond to any atom so long as appropriate valences are maintained:

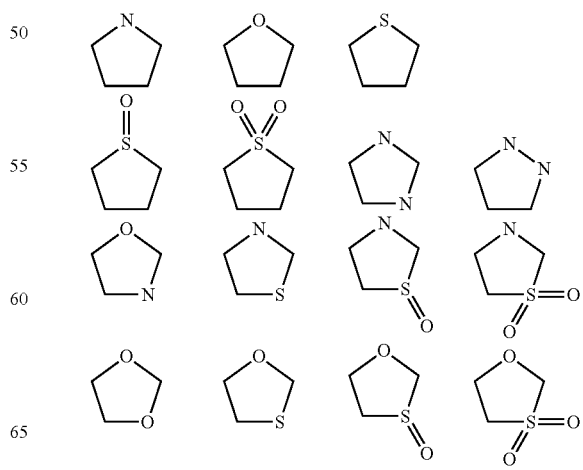

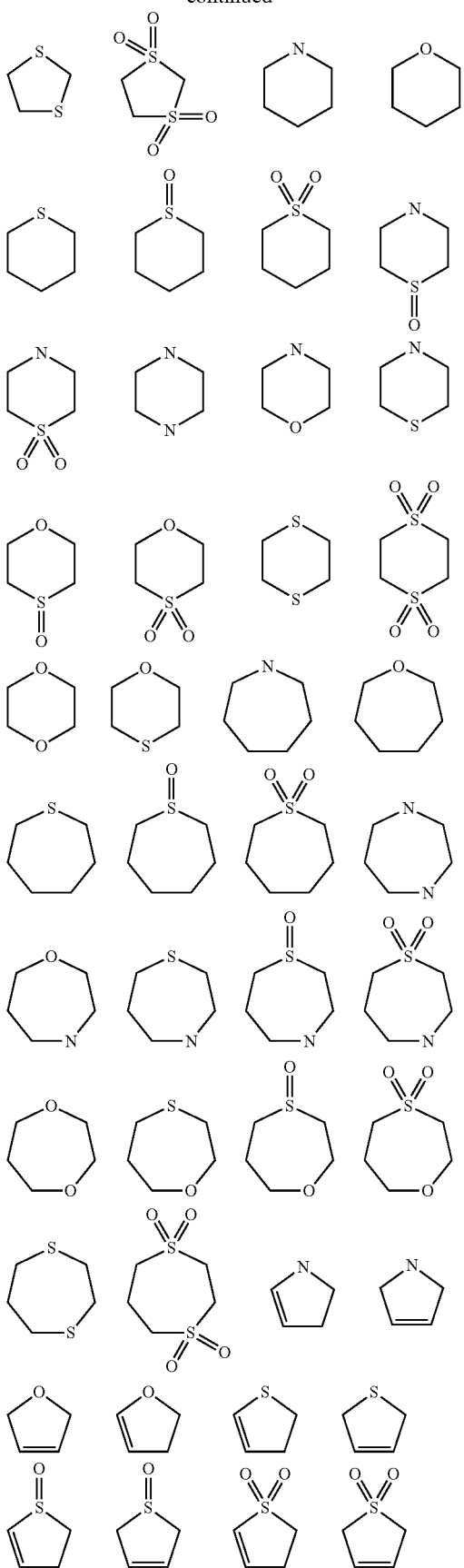
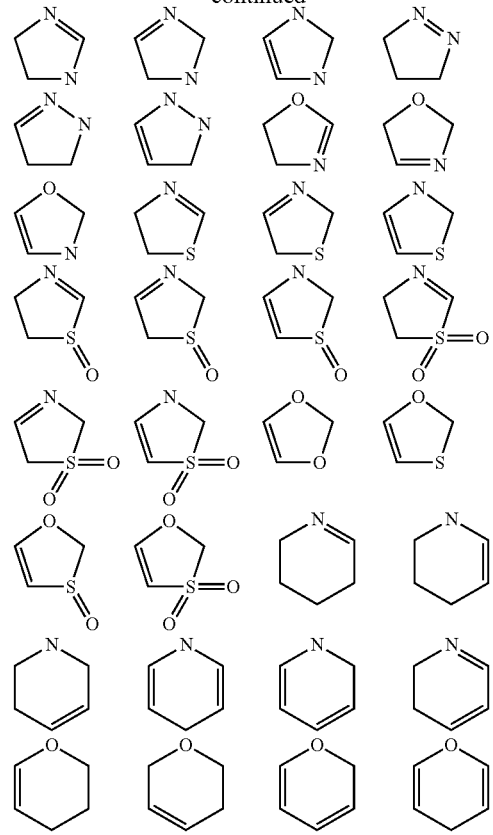
Thus, the term "monocyclic $C_{5-6}$-heteroaryl" includes the following exemplary structures which are not depicted as radicals as each form may be attached through a covalent bond to any atom so long as appropriate valences are maintained:
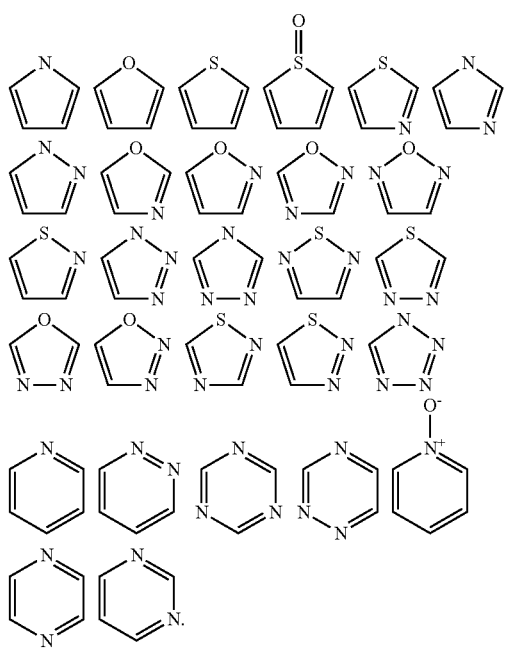

The term "bicyclic $C_{8-10}$-heterocyclyl" means a saturated or unsaturated bicyclic-ring system including aromatic ring systems containing one or more heteroatoms selected from N, O or $S(O)_r$, wherein r=0, 1 or 2, consisting of 8 to 10 ring atoms wherein the heteroatoms are optionally part of the aromatic ring. The term "bicyclic $C_{8-10}$-heterocyclyl" is intended to include all the possible isomeric forms.

Thus, the term "bicyclic $C_{8-10}$-heterocyclyl" includes the following exemplary structures which are not depicted as radicals as each form may be attached through a covalent bond to any atom so long as appropriate valences are maintained:

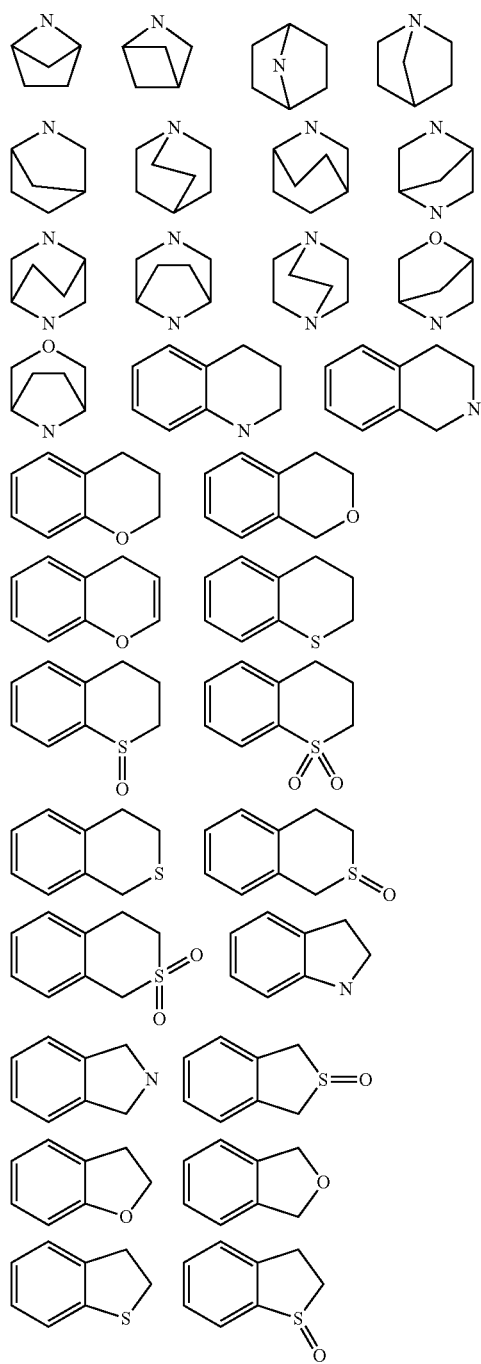

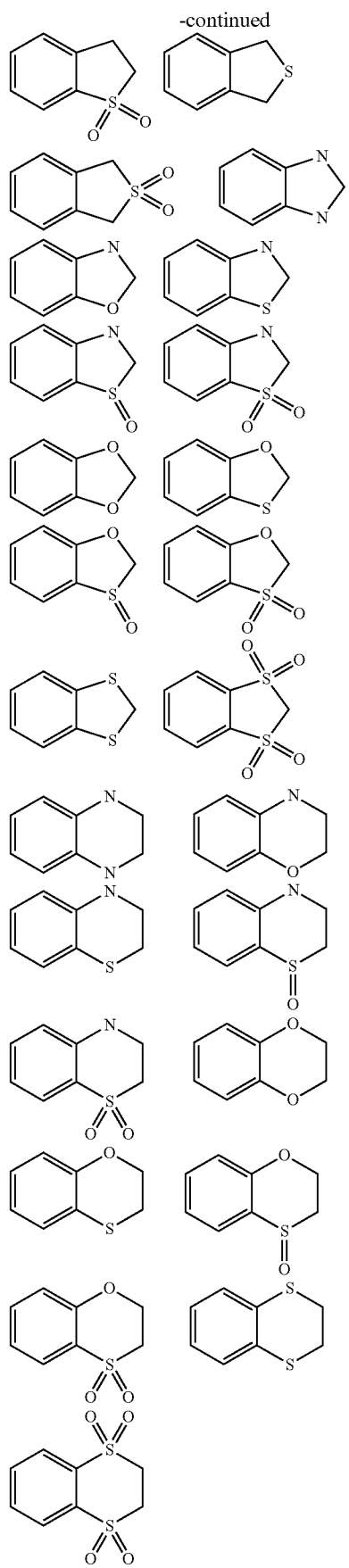

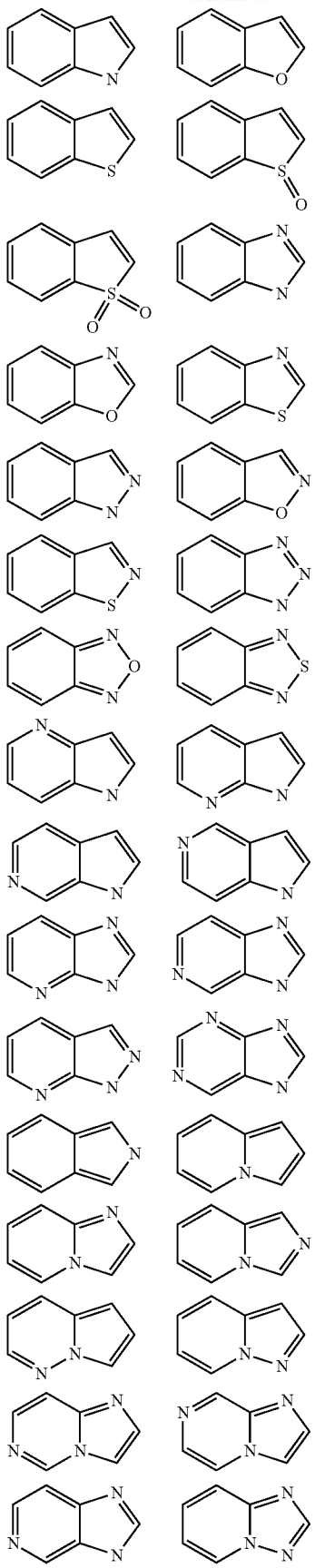

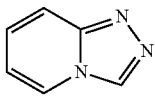

The term "annelated species of aryl or heterocyclyl" as used herein, either alone or in combination with another substituent wherein the annelated species presents as an aryl-het (a), a hetaryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes $-CH_2-$, $-CH_2-CH_2-$, $-CH(CH_3)-$, $-CH_2-CH_2-CH_2-$, $-C(CH_3)_2-$, $-CH(CH_2CH_3)-$, $-CH(CH_3)-CH_2-$, $-CH_2-CH(CH_3)-$, $-CH_2-CH_2-CH_2-CH_2-$, $-CH_2-CH_2-CH(CH_3)-$, $-CH(CH_3)-CH_2-CH_2-$, $-CH_2-CH(CH_3)-CH_2-$, $-CH_2-C(CH_3)_2-$, $-C(CH_3)_2-CH_2-$, $-CH(CH_3)-CH(CH_3)-$, $-CH_2-CH(CH_2CH_3)-$, $-CH(CH_2CH_3)-CH_2-$, $-CH(CH_2CH_2CH_3)-$, $-CH(CH(CH_3))_2-$ and $-C(CH_3)(CH_2CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkenylene" is used for a group as defined in the definition for "$C_{1-n}$-alkylene" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{2-n}$-alkynylene" is used for a group as defined in the definition for "$C_{1-n}$-alkylene" with at least two carbon atoms, if at least two of those carbon atoms of said group are bonded to each other by a triple bond.

By the term "$C_{1-6}$-alkoxy" (including those which are part of other groups) are meant branched and unbranched alkoxy groups with 1 to 6 carbon atoms and by the term "$C_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "$C_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

In all cases of contradictions between structure and their naming, structure shall prevail.

5. PREFERRED EMBODIMENTS

The substituent $R^1$ denotes H or methyl, preferably hydrogen.

The substituent $R^2$ is selected from a group consisting of H, $C_{1-4}$-alkyl, $C_{1-4}$-alkyl-O—CO—, $C_{1-4}$-alkyl-O—CO—$C_{1-4}$-alkyl-, $C_{1-4}$-alkyl-O—$C_{1-4}$-alkyl-, HO—CO— and HO—CO—$C_{1-4}$-alkyl-, preferably methyl and hydrogen, particularly preferred hydrogen.

The substituent $R^3$ denotes H or methyl, preferably hydrogen.

The substituent $R^4$ denotes H or methyl, preferably hydrogen, or
the substituents $R^3$ and $R^4$ together form an ethylene bridge.
Variables m, n independently from each other with the proviso that (m+n)<4, denote 0, 1 or 2, preferably with the proviso that 0<(m+n)<4 denote 0, 1 or 2, particularly preferred denote m=n=1, The symbol X denotes halogen, preferably Cl or Br, particularly preferred Cl.

The symbol $L^1$ denotes a bond or is selected from the group consisting of
—CH$_2$—, —CH$_2$—CH$_2$—, —CH$_2$O—, —CO—, —S—, —SO—, —SO$_2$—, —S—CH$_2$—, SO—CH$_2$— and —SO$_2$—CH$_2$—, preferably a bond, —CH$_2$— and —CH$_2$—CH$_2$—, particularly preferred a bond.

The symbol $Y^1$ denotes a C-linked five- or six-membered heteroaromatic moiety or a C-linked 8-10-membered heteroaromatic moiety, each substituted by $R^5$, $R^6$, $R^7$ and $R^8$, preferably $Y^1$ is selected from a group consisting of a linker of formula (a1) to (z1)

(a1)

(b1)

(c1)

(d1)

(e1)

(f1)

(g1)

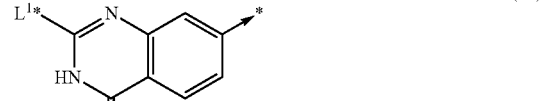

(h1)

(i1)

(k1)

(l1)

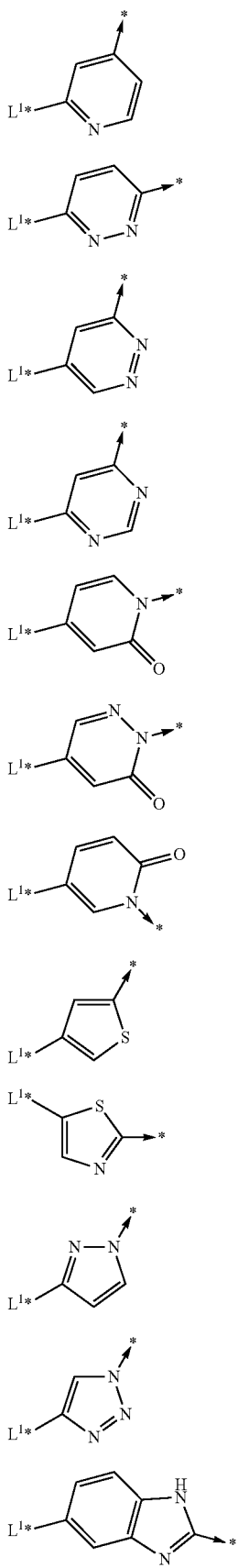

preferably of formula (a1) to (k1).

\* denotes the attachment point to a substituent of $Y^1$ $L^1$* denotes the attachment point to $L^1$ The substituent $R^7$ is selected from a group consisting of H, halogen, CN, $C_{1-4}$-alkyl-, optionally substituted by one or more F atoms, HC≡C—, OH, $C_{1-4}$-alkyl-O— and HO—CH$_2$—, preferably hydrogen, F, Cl. and methyl, particularly preferred hydrogen.

The substituent $R^8$ is selected from a group consisting of H, halogen, CN, $C_{1-4}$-alkyl-, optionally substituted by one or more F atoms, HC≡C—, OH, $C_{1-4}$-alkyl-O— and HO—CH$_2$—, preferably hydrogen, F, Cl. and methyl, particularly preferred hydrogen.

The substituent $R^5$ is selected from a group consisting of H, halogen, =O, CN, N$_3$, $C_{1-4}$-alkyl-, optionally substituted by one or more F atoms,
HC≡C—, OH, $C_{1-4}$-alkyl-O—, HO—CH$_2$—,
H$_2$C=CH—CH$_2$—O—, HC≡C—CH$_2$—, HC≡C—CH$_2$—O—, —NR$^{5.1}$R$^{5.2}$,
H$_2$N—C(NH)—, H$_2$N—C(NH)NH—, H$_2$N—C(NH)NH—CH$_2$—, —COOH, $C_{1-4}$-alkyl-OCO—,
—$C_{1-4}$-alkyl-COOH, —$C_{1-4}$-alkyl-COO—$C_{1-4}$-alkyl,
—OCH$_2$—COOH, —OCH$_2$—COO—$C_{1-4}$-alkyl, and
—B(OH)$_2$,
preferably hydrogen, F, Cl, =O, methyl, ethyl and methoxy, particularly preferred hydrogen.

The substituent $R^{5.1}$ denotes H, $C_{1-4}$-alkyl-, $C_{1-4}$-alkyl-CO— or $C_{1-4}$-alkyl-SO$_2$—, preferably hydrogen, methyl, or acetyl.

The substituent $R^{5.2}$ denotes H or $C_{1-4}$-alkyl-, preferably hydrogen or methyl.

The substituents $R^{5.1}$ and $R^{5.2}$ together with the nitrogen atom they are attached to may form an optionally substituted 4-7-membered heterocycle containing at least one N-atom, preferably pyrrolidine, morpholine, piperazine or 2-pyridon-1-yl.

The substituent $R^6$ denotes -$L^2$-$Y^2$-$L^3$-$R^{6.5}$ or is selected from a group consisting of
H, halogen, =O, CN, N$_3$, $C_{1-4}$-alkyl-, optionally substituted by one or more F atoms,
HC≡C—, OH, $C_{1-4}$-alkyl-O—, HO—CH$_2$—,
H$_2$C=CH—CH$_2$—O—, HC≡C—CH$_2$—, HC≡C—CH$_2$—O—, —NR$^{6.1}$R$^{6.2}$,
H$_2$N—C(NH)—, H$_2$N—C(NH)NH—, H$_2$N—C(NH)NH—CH$_2$—, —COOH, $C_{1-4}$-alkyl-OCO—,
—$C_{1-4}$-alkyl-COOH, —$C_{1-4}$-alkyl-COO—$C_{1-4}$-alkyl,
—OCH$_2$—COOH, —OCH$_2$—COO—$C_{1-4}$-alkyl, and
—B(OH)$_2$,
preferably —$C_{1-4}$-alkyl-COO—$C_{1-4}$-alkyl, —OCH$_2$—COO—$C_{1-4}$-alkyl, $C_{1-4}$-alkyl-OCO—, HC≡C—, halogen, HC≡C—CH$_2$—, —$C_{1-4}$-alkyl-COOH, —OCH$_2$—COOH and —COOH, especially preferred —COOH, $C_{1-4}$-alkyl-COOH, —OCH$_2$—COOH, —C$_{1-4}$-alkyl-COO-methyl, —OCH$_2$—COO-methyl, methyl-OCO—, particularly preferred —COOH and methyl-OCO—, wherein, the substituent R$^{6.1}$ denotes H, C$_{1-4}$-alkyl-, C$_{1-4}$-alkyl-CO— or C$_{1-4}$-alkyl-SO$_2$—, preferably hydrogen, methyl or acetyl.

the substituent R$^{6.2}$ denotes H or C$_{1-4}$-alkyl-, preferably hydrogen or methyl.

or

R$^{6.1}$ and R$^{6.2}$ together with the nitrogen atom they are attached to form an optionally substituted 4-7-membered heterocycle containing at least one N-atom, preferably pyrrolidine, morpholine, piperazine or 2-pyridon-1-yl.

Most preferably the substituent R$^6$ denotes -L$^2$-Y$^2$-L$^3$-R$^{6.5}$.

Particularly preferred, the substituent R$^6$ denotes —COOH or C$_{1-4}$-alkyl-OCO—Y$^1$ is selected from among (a1), (b1), (d1), (e1) and (g1).

The symbol L$^2$ denotes a bond or is selected from a group consisting of —CH$_2$—, —CH$_2$—CH$_2$—, and —CH$_2$—CO—, or, with the proviso that L$^2$ is attached to a carbon atom of Y$^1$, is selected from a group consisting of —O—, —CH$_2$—O—, —O—CH$_2$—, —CO—, —CO—CH$_2$—, —S—, —SO—, —SO$_2$— and —O—CO—. Preferably L$^2$ denotes a bond, —CH$_2$— or —CH$_2$—CH$_2$— particularly preferred a bond.

The symbol Y$^2$ denotes a bond or is selected from a group consisting of

Y$^{2.1}$, —CO—, —NR$^{11}$—CO—, —CO—NR$^{11}$—, —Y$^{2.1}$—CONR$^{11}$—, —Y$^{2.1}$—CO— and —NR$^{11}$—CO—Y$^{2.1}$—, preferably Y$^{2.1}$, —CO—, —CO—NR$^{11}$—, particularly preferred —CO—NR$^{11}$— with the proviso that carbonyl moieties are not directly attached to nitrogen atoms of unsaturated heterocycles and are not directly attached to another carbonyl moiety.

The substituent R$^{11}$ denotes -L$^4$-R$^9$.

The symbol Y$^{2.1}$ denotes a cyclic linker selected from either a phenylene group optionally substituted by -L$^5$R$^{10}$, or an optionally substituted heteroaromatic or heterocyclic moiety each containing at least one nitrogen atom.

Preferably Y$^{2.1}$ is selected from a group consisting of a linker of formula (a2) to (k2), preferably of formula (c2), (d2), (e2), and (f2)

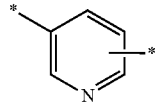  (a2)

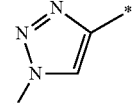  (b2)

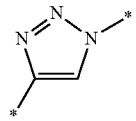  (c2)

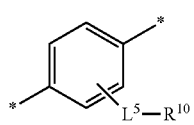  (d2)

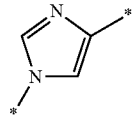  (e2)

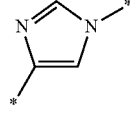  (f2)

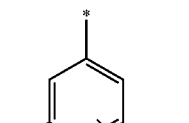  (g2)

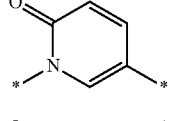  (h2)

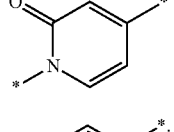  (i2)

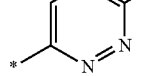  (j2)

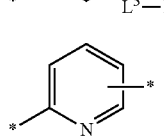  (k2)

The symbols L$^3$, L$^4$, L$^5$ independently from each other denote a bond or a linear chain of formula (m)

—(CH$_2$)$_i$—[O—(CH$_2$)$_{g1}$]$_{p1}$—[O—(CH$_2$)$_{g2}$]$_{p2}$—  (m)

wherein i denotes 0, 1, 2 or 3, preferably 0, 1 or 2 g1, g2 independently from each other denote 2 or 3, preferably 2, p1, p2 independently from each other denote 0, 1, 2 or 3, preferably 0, 1 or 2 with the provisio that the linear chain is consisting of 1 to 12 moieties selected from a group consisting of —CH$_2$—, and —O—.

Particularly preferred L$^3$ denotes bond, —(CH$_2$)—, —(CH$_2$)$_2$—, —(CH$_2$)$_2$—[O—(CH$_2$)$_2$]—, —(CH$_2$)$_2$[O—(CH$_2$)$_2$]$_2$—, or —(CH$_2$)$_2$—[(CH$_2$)$_2$]$_3$—

Particularly preferred L$^4$ denotes a bond, —(CH$_2$)—, or —(CH$_2$)$_2$—.

Particularly preferred L$^5$ denotes a bond or —O—(CH$_2$)$_2$—.

The substituents R$^{6.5}$, R$^9$, R$^{10}$ independently from each other are selected from a group consisting of H, halogen, CN, C$_{1-4}$-alkyl, HC≡C—, OH, C$_{1-4}$-alkyl-O—, HO—CH$_2$—, H$_2$C═CH—CH$_2$—O—, HC≡C—

CH₂—O—, B(OH)₂, BF₃⁻, —S(O)₂OH, —C(CH₂OH)₃, —CH(CH₂OH)₂, and —CH(OH)CH₂OH or denote a five- or six membered heteroaromatic or heterocyclic moiety, optionally substituted by one or two substituents independently selected from halogen, CN, C₁₋₄-alkyl-, optionally substituted by one or more F atoms, HC≡C—, OH, C₁₋₄-alkyl-O—, HO—CH₂—, Preferably the substituents $R^{6.5}$, $R^9$, $R^{10}$ independently from each other denote a moiety selected from a group consisting of 2-pyridyl, 3-pyridyl, 4-pyridyl, 2-pyridon-1-yl, 3-pyridazinon-2-yl, 3-pyridazinyl, 1-pyrrolidinyl, 1-piperidinyl, 1-morpholinyl, 1-piperazinyl, 4-acetyl-piperazinyl, and 4-oxo-1-thiomorpholinyl.

each optionally substituted by up to two substituents independently selected from halogen, CN, C₁₋₄-alkyl-, optionally substituted by one or more F atoms, HC≡C—, OH, C₁₋₄-alkyl-O—, HO—CH₂—, preferably OH, Particularly preferred the substituent $R^{6.5}$ denotes H, OH or pyridyl.

Particularly preferred the substituent $R^9$ denotes H or OH.

Particularly preferred the substituent $R^{10}$ denotes H or OH.

Any and each other of the substituents defined above may be combined with each other.

6. PREPARATION

The following methods are suitable for preparing compounds of general formula (I).

The compounds according to the invention may be obtained using methods of synthesis which are known to the one skilled in the art and described in the literature of organic synthesis. General methods for functional groups protection and deprotection steps are described e.g. in: *Greene, T. W. and Wuts, P. G. M. (eds.): Protective Groups in Organic Synthesis, third edition* 1999; *John Wiley and Sons, inc*. Preferably the compounds are obtained analogously to the methods of preparation explained more fully hereinafter, in particular as described in the experimental section.

Compounds of general formula I can be prepared by reacting S-methylisothioureas of formula II with primary amines of formula III in a solvent like THF, acetonitrile or DMF or in a solvent mixture, preferably in the presence of a base, especially when the primary amine III is applied as an acid addition salt, preferably at r.t.

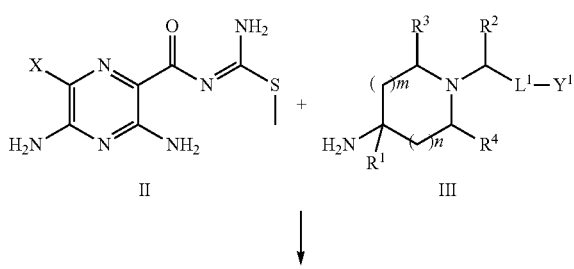

Compounds of general formula II can be prepared by reacting S-methylisothiourea (which may be generated in situ from its sulphuric acid salt by addition of base) with a 1-(tert-butylcarbamoyl)prop1-en-2-yl carboxylate of general formula IV in a solvent like DCM, THF, TBME, water or a mixture of these solvents, preferably at r.t. Compounds of general formula IV can be prepared from the respective carboxylic acid of general formula V and a 2-tert-butyl-5-methyl-isoxazolium salt of general formula VI, which can be applied as an isolated salt (e.g. the hexafluorophosphate salt; X=PF₆) or generated in situ from tert-butanol, 5-methylisoxazole and trifluoromethanesulphonic acid. The latter reaction is preferably performed in a solvent like DMF or in a solvent mixture with the addition of triethylamine or an other base, preferably while cooling to 0-10° C.

Compounds of general formula III can be prepared from compounds of general formula VII by removal of the respective protecting group PG, preferably the BOC (tert-Butoxycarbonyl) or FMOC (9H-Fluoren-9-yl-methoxycarbonyl) protecting group which can be removed by standard acicid or basic conditions, respectively. Compounds of general formula VII can be modified using methods of synthesis which are known to one skilled in the art and described in the literature of organic synthesis, preferably by functional group protection or deprotection steps, esterifications, amidations, hydrogenations, or 1,3-dipolar cycloadditions of an azide to a terminal alkyne group or vice versa. Thereby, before such a modification, the structure of $Y^1$ may be beyond what is claimed hereinafter. Compounds of general formula VII can be prepared from secondary amines of general formula VIII, preferably either by alkylation with a compound of general formula IX (wherein the leaving group LG is preferably Cl, Br, OMesyl, or OTosyl), or by reductive amination with an aldehyde of general formula X (wherein $R^2$=H).

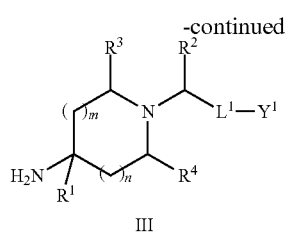

III

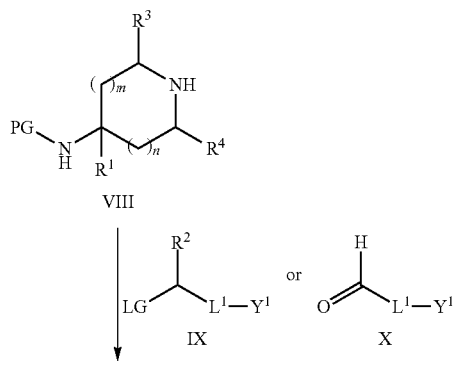

Compounds of general formula I can be converted into intermediates of general formula XI by BOC-protection. Compounds of general formulas I or XI can be modified using methods of synthesis which are known to the one skilled in the art and described in the literature of organic synthesis, preferably by functional group protection or deprotection steps, esterifications, amidations, hydrogenations, or 1,3-dipolar cycloadditions of an azide to a terminal alkyne group or vice versa. Thereby, before such a modification, the structures of $R^2$ and $Y^1$ may be beyond of what is claimed hereinafter. After such modification steps, the BOC protecting group in compounds of general formula XI can removed again by standard acidic deprotection conditions to yield modified compounds of general formula I.

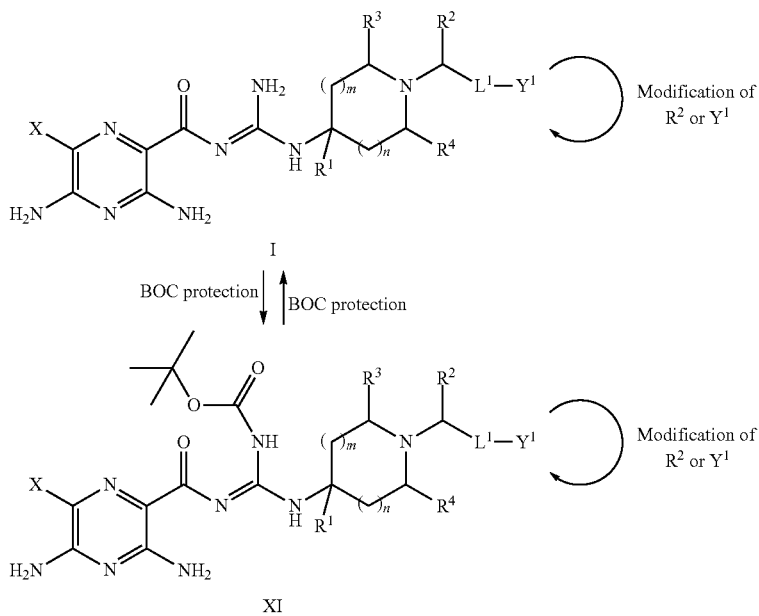

-continued

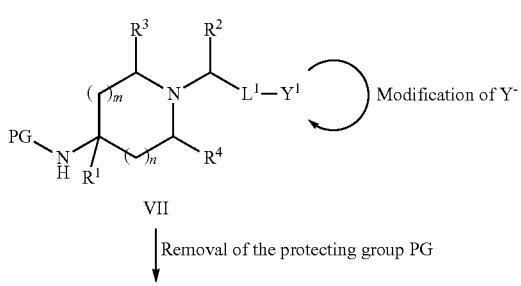

7. EXAMPLES

Where no salt form of a compound is specified, the compound may exist as a free base or a salt, depending on the synthesis conditions and the processes of workup and purification applied. The skilled person will appreciate that the compound is not limited to the free base or a certain salt form. Where a salt form of a compound is specified, the stoichiometry of the counterion is usually omitted. The skilled person will appreciate that the compound is not limited to the mono salt and that it may exist as a disalt, trisalt or other compound: counterion stoichiometries. Furthermore, the skilled person will appreciate that such compound may unexpectedly exist

7.1 SYNTHESIS OF INTERMEDIATES

Intermediate A.1

3,5-diamino-6-chloropyrazine-2-carboxylic acid

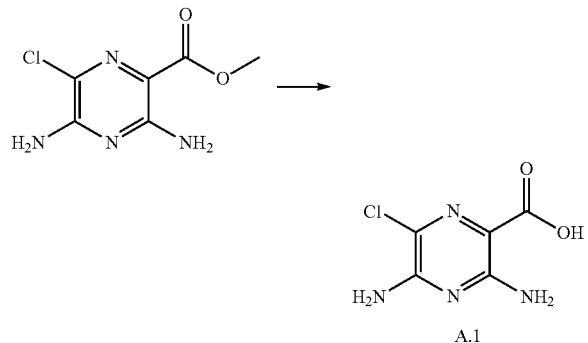

A mixture of methyl 3,5-diamino-6-chloropyrazine-2-carboxylate (100 g; 494 mmol), methanol (1 l) and NaOH (6 mol/l in water; 240 mL; 1.44 mol) is refluxed for 3 h. The mixture is allowed to cool to r.t. and then neutralized by addition of hydrochloric acid (6 mol/l in water; approx. 240 mL). Water (200 mL) is added. The precipitate formed is filtered off with suction, washed with water and dried at 60° C.

$C_5H_5ClN_4O_2$ ESI Mass spectrum: m/z=189 [M+H]+; m/z=187 [M−H]−

Intermediate A.2

3,5-Diamino-6-bromopyrazine-2-carboxylic acid is prepared from methyl 3,5-diamino-6-bromopyrazine-2-carboxylate (which is prepared from methyl 3,5-diamino-6-chloropyrazine-2-carboxylate as described in J. Med. Chem. 10 (1967) 66-75) analogously to the procedure described for the synthesis of intermediate A.1

Intermediate B.1

1-(tert-Butylcarbamoyl)prop-1-en-2-yl 3,5-diamino-6-chloropyrazine-2-carboxylate

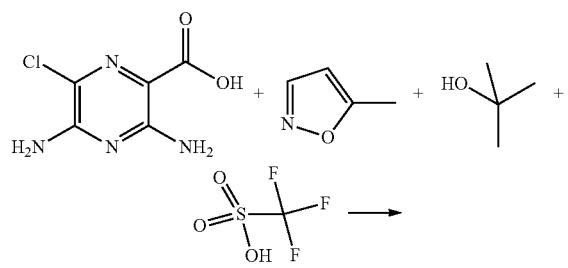

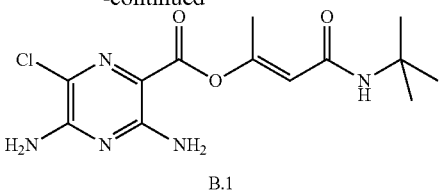

Stage 1:
A mixture of tert-butanol (21.0 mL; 226 mmol) and 5-methylisoxazole (18.0 mL; 221 mmol) is cooled with an ice-bath. Trifluoromethanesulphonic acid (20.0 mL; 221 mmol) is added dropwise with continued cooling. The resulting mixture is stirred for 1 h without further cooling.

Stage 2:
To a solution or suspension of 3,5-diamino-6-chloropyrazine-2-carboxylic acid (intermediate A.1; 14.0 g; 74.2 mmol) and triethylamine (31.0 mL; 222 mmol) in DMF (100 mL) is added the mixture prepared in stage 1. The resulting mixture is stirred for 4 h at r.t. Ice-water is added with stirring. The precipitate formed is filtered off with suction, washed with water and dried at 65° C. to yield the title compound.

$C_{13}H_{18}ClN_5O_3$ ESI Mass spectrum: m/z=328 [M+H]+; m/z=326 [M−H]−

TLC (Silica; DCM/MeOH 9:1): $R_f$=0.4

Intermediate B.2

1-(2-Methyl-2-butyl-carbamoyl)prop-1-en-2-yl 3,5-diamino-6-bromopyrazine-2-carboxylate

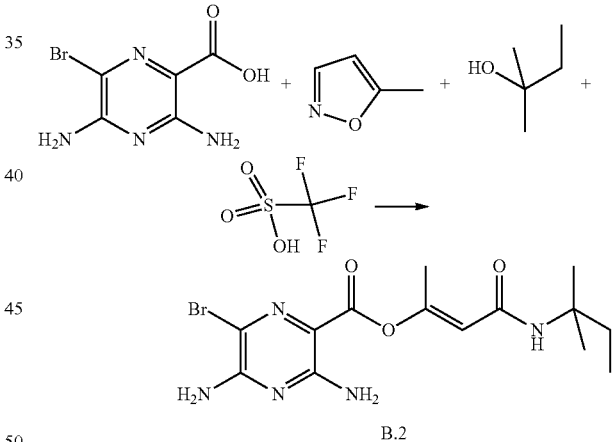

Stage 1:
A mixture of 2-methyl-2-butanol (5.75 mL; 51 mmol) and 5-methylisoxazole (4.42 mL; 51 mmol) is cooled with an ice-bath. Trifluoromethanesulphonic acid (4.84 mL; 54 mmol) is added dropwise with continued cooling. The resulting mixture is stirred over night without further cooling.

Stage 2:
To a solution or suspension of 3,5-diamino-6-bromopyrazine-2-carboxylic acid (Intermediate A.2; 5.00 g; 21.5 mmol) and triethylamine (7.48 mL; 54 mmol) in DMF (50 mL) cooled with an ice-bath is added dropwise the mixture prepared in stage 1. The resulting mixture is stirred for 4 h at r.t., then poured on ice-water. The precipitate formed is filtered off with suction, washed with water and dried at 50° C. to yield the title compound.

$C_{14}H_{20}BrN_5O_3$ ESI Mass spectrum: m/z=386 [M+H]+; m/z=384 [M−H]−

Intermediate C.1

3,5-diamino-6-chloro-N-[(methylsulfanyl)methanimidoyl]pyrazine-2-carboxamide

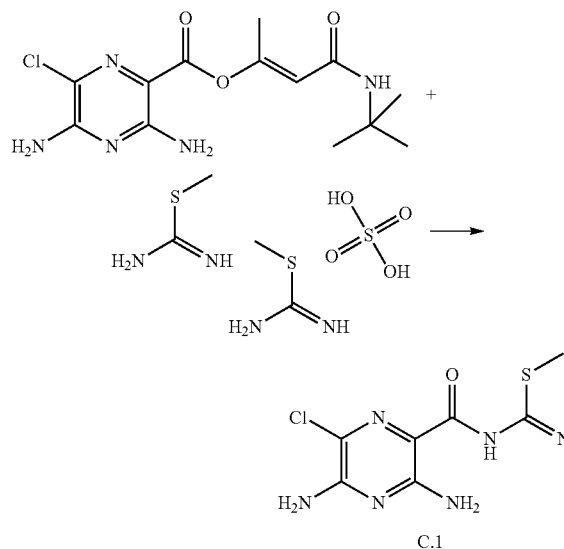

C.1

To NaOH (1 mol/l in water; 9.2 mL; 9.2 mmol) is added S-methylisothiourea sulphate (1.78 g; 6.1 mmol. The mixture is stirred until complete solution is achieved. TBME/THF (1:1; 30 mL) and then 1-(tert-butylcarbamoyl)prop-1-en-2-yl 3,5-diamino-6-chloropyrazine-2-carboxylate (Intermediate B.1; 2.00 g; 6.10 mmol) are added and the mixture is stirred at r.t. over night, then water (6 mL) is added. The precipitate formed is filtered off with suction, washed successively with water, methanol and then with diethyl ether and then dried at 50° C. to yield the title compound.

$C_7H_9ClN_6OS$ ESI Mass spectrum: m/z=261 [M+H]+; m/z=259 [M−H]−

Intermediate C.2

3,5-diamino-6-bromo-N-[(methylsulfanyl)methanimidoyl]pyrazine-2-carboxamide

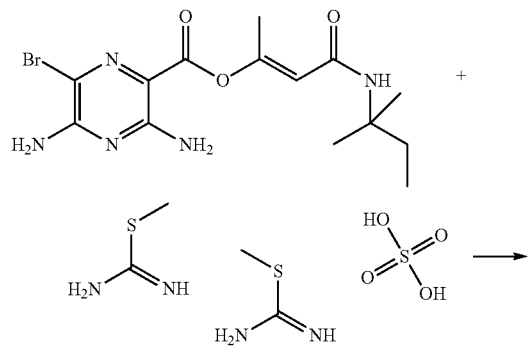

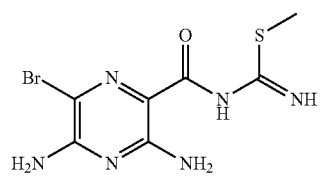

C.2

To NaOH (1 mol/l in water; 30 mL; 30 mmol) is added S-methylisothiourea sulphate (5.42 g; 19.5 mmol). The mixture is stirred until complete solution is achieved. TBME/THF (1:1; 100 mL) and then 1-(2-methyl-2-butyl-carbamoyl)prop-1-en-2-yl 3,5-diamino-6-bromopyrazine-2-carboxylate (Intermediate B.2; 7.52 g; 19.5 mmol) are added and the mixture is stirred at r.t. over night, then water (100 mL) is added. The precipitate formed is filtered off with suction, washed with THF/water (1:2) and then dried at 50° C. to yield the title compound.

$C_7H_9BrN_6OS$ ESI Mass spectrum: m/z=305 [M+H]+

Intermediate I.1

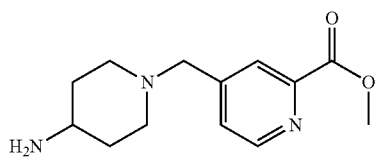

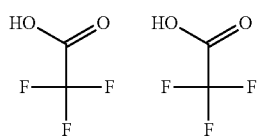

I.1

A mixture of the respective BOC-protected compound (XIV.1)(2.00 g; 5.72 mmol), TFA (4.42 ml; 57.1 mmol) and DCM (50 ml) is stirred for 3 h at r.t. Volatiles are evaporated and the residue is triturated with TBME, filtered off with suction and dried in vacuo to yield the title compound as a TFA salt.

$C_{13}H_{19}N_3O_2 \times 2$ TFA ESI Mass spectrum: m/z=250 [M+H]+

The following intermediates of general formula I.A are prepared accordingly from the respective BOC-protected compounds of general formula I.B as indicated. Products obtained as an oil are applied to subsequent syntheses without prior trituration. Due to conditions applied, the syntheses may yield a free base, a hydrochloride or dihydrochloride salt, a zwitterion or other salt forms which can be applied equally to the syntheses of example compounds described below.

| Intermediate | Y¹ | starting material | Synthesis comment |
|---|---|---|---|
| I.2 | (4-pyridyl)-C(O)-N(CH₂CH₂OH)₂ | II.1 | |
| I.3 | imidazo[1,2-a]pyridin-2-yl with 6-C(O)NH-CH₂CH₂-O-CH₂CH₂OH | II.2 | |
| I.4 | 5-pyridyl-2-(CH₂CH₂-3-pyridyl) | III.1 | |
| I.5 | 5-(2-oxo-1-(pyridin-3-ylmethyl)pyridin-1(2H)-yl) | IV.1 | |
| I.6 | imidazo[1,2-a]pyridin-2-yl, 6-C(O)OMe | VI.1 | |
| I.7 | imidazo[1,2-a]pyridin-2-yl, 6-C(O)NH-CH₂CH₂OH | II.3 | |
| I.8 | 4-oxo-3,4-dihydroquinazolin-2-yl | XIX.1 | reaction at 50° C. |
| I.9 | 5-(methoxycarbonyl)thiophen-2-yl | VI.2 | |
| I.10 | 5-((trimethylsilyl)ethynyl)pyridin-3-yl | V.1 | reaction in HCl/dioxane |

| Intermediate | Y¹ | starting material | Synthesis comment |
|---|---|---|---|
| I.11 | imidazo[1,2-a]pyridine with I substituent | VI.3 | |
| I.12 | pyridine-2-carboxamide with -NH-CH₂CH₂-O-CH₂CH₂-OH | II.4 | |
| I.13 | 2-oxo-pyridinyl with N-propargyl | XVII.1 | |

Intermediate II.1

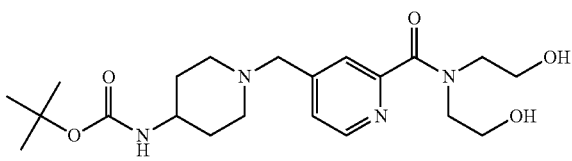

II.1

A mixture of 4-(4-tert-butoxycarbonylamino-piperidin-1-ylmethyl)-pyridine-2-carboxylic acid (XIII.1) (0.30 g; 0.89 mmol), TBTU (345 mg; 1.08 mmol) and DIPEA (180 μl; 1.0 mmol) in DMF (5 mL) is stirred for 20 min. The amine 2-(2-hydroxy-ethylamino)-ethanol (100 μl; 1.1 mmol) is added and the mixture is stirred over night. Sodium carbonate and water are added and the mixture is extracted with DCM. The organic layer is dried with MgSO₄, filtered and evaporated. The residue is reevaporated with TBME.

$C_{21}H_{34}N_4O_5$ ESI Mass spectrum: m/z=423 [M+H]⁺; m/z=467 [M+HCOO]⁻

The following intermediates of general formula II.A are prepared accordingly from the respective carboxylic acids and amines as indicated. Depending on conditions applied, the syntheses may yield a free base, a TFA salt or other salt forms which can be applied equally to the syntheses of example compounds described below.

| Example | Y¹ | Carboxylic acid applied | amine applied | Synthesis comment |
|---|---|---|---|---|
| II.2 | imidazo[1,2-a]pyridin-2-yl connected to 6-C(=O)NH-CH₂CH₂-O-CH₂CH₂-OH | XV.1 | H₂N-CH₂CH₂-O-CH₂CH₂-OH | Purified by RP HPLC (column: Xbridge; water-MeOH; modifier NH₃) |

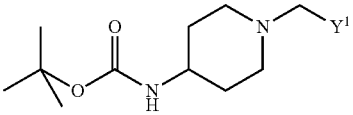

| Example | Y¹ | Carboxylic acid applied | amine applied: | Synthesis comment |
|---|---|---|---|---|
| II.3 | 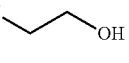 | XV.1 | H₂N-CH₂CH₂-OH | Purified by RP HPLC (column: Xbridge; water-MeOH; modifier NH₃) |
| II.4 | 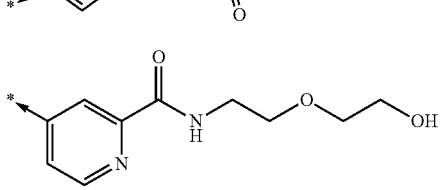 | XIII.1 | H₂N-CH₂CH₂-O-CH₂CH₂-OH | |

Intermediate III.1

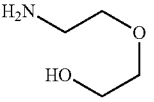

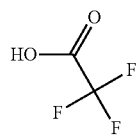

A mixture of [1-(6-pyridin-3-ylethynyl-pyridin-3-ylmethyl)-piperidin-4-yl]-carbamic acid tert-butyl ester (XI.1) (0.145 g; purity 80% 0.23 mmol), 20 mg Raney Nickel and 10 mL methanol is hydrogenated at 50 PSI and r.t. for 3 h. The mixture is filtered and evaporated. The residue is purified via RP-HPLC (column: sunfire; water-MeOH; modifier TFA).

$C_{23}H_{32}N_4O_2$ ESI Mass spectrum: m/z=397 [M+H]⁺; m/z=297 [M+2H—BOC]⁺

Intermediate IV.1

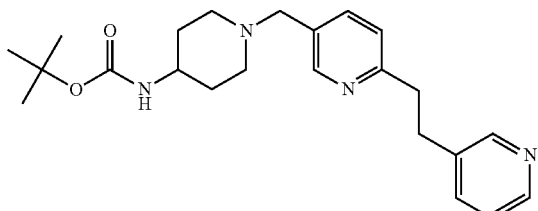

A mixture of [1-(6-oxo-1-pyridin-3-ylmethyl-1,6-dihydro-pyridin-3-carboxaldehyde (X.1) (0.550 g; 2.57 mmol), BOC-4-aminopiperidine (520 mg; 2.60 mmol) and 10 mL THF is refluxed 1 h. The pH is adjusted with acetic acid to pH 4-5, sodium triacetoxyborohydride (700 mg; 3.30 mmol) is added and the mixture is refluxed over night. Water is added and the mixture is extracted with ethyl acetate. The organic layer is dried with MgSO₄, filtered and evaporated. The residue is purified by silica gel column chromatography (gradient: DCM/methanol 3-10%). $C_{22}H_{30}N_4O_3$ ESI Mass spectrum: m/z=399 [M+H]⁺; m/z=443 [M+HCOO]⁻

Intermediate V.1

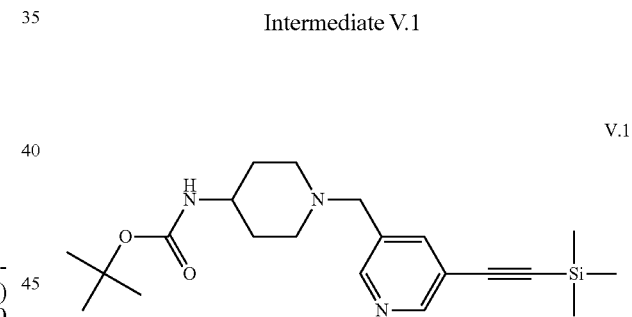

To a solution of (5-trimethylsilanylethynyl-pyridin-3-yl)-methanol (VIII.1) (4.6 g; 15.23 mmol), triethylamine (4.3 mL; 30.47 mmol) and 40 mL DCM, methanesulfonyl chloride (1.8 mL; 22.85 mmol) is added slowly and the mixture is stirred over night at r.t. Water is added, followed by an extraction. The organic layer is dried with MgSO₄, filtered and evaporated. The residue is dissolved in 30 mL ACN, BOC-4-aminopiperidine (3.36 g; 16.76 mmol) and triethylamine (4.3 mL; 30.47 mmol) are added and the mixture is stirred 3 h at 70° C. The mixture is evaporated and ethyl acetate and water are added to the residue followed by an extraction. The organic layer is dried with MgSO₄, filtered and evaporated. The residue is purified by silica gel column chromatography (gradient: DCM/methanol 0-10%).

$C_{21}H_{33}N_3O_2Si$ ESI Mass spectrum: m/z=388 [M+H]⁺; m/z=432 [M+HCOO]⁻

Intermediate VI.1

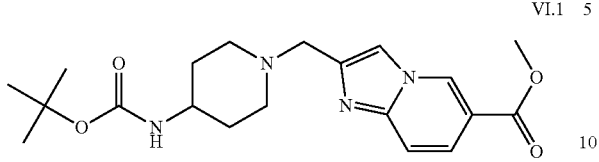

To a solution of 2-chloromethyl-imidazo[1,2-a]pyridine-6-carboxylic acid methyl ester (IX.1). (1.48 g; 6.59 mmol) in 30 mL ACN, potassium carbonate (1.82 g; 13.18 mmol) and BOC-4-aminopiperidine (1.39 g; 6.92 mmol) are added and the mixture is stirred over night at r.t. Water and ethyl acetate are added, followed by an extraction. The organic layer is dried with $MgSO_4$, filtered and evaporated. The residue is purified by silica gel column chromatography (gradient: DCM/(methanol/aqueous ammonia 9:1) 0-10%).

$C_{20}H_{28}N_4O_4$ ESI Mass spectrum: m/z=389 $[M+H]^+$; m/z=387 $[M-H]^-$

The following intermediates of general formula VI.A are prepared accordingly from the respective chloromethyl intermediate as indicated. Depending on conditions applied, the syntheses may yield a free base, a TFA salt or other salt forms which can be applied equally to the syntheses of example compounds described below.

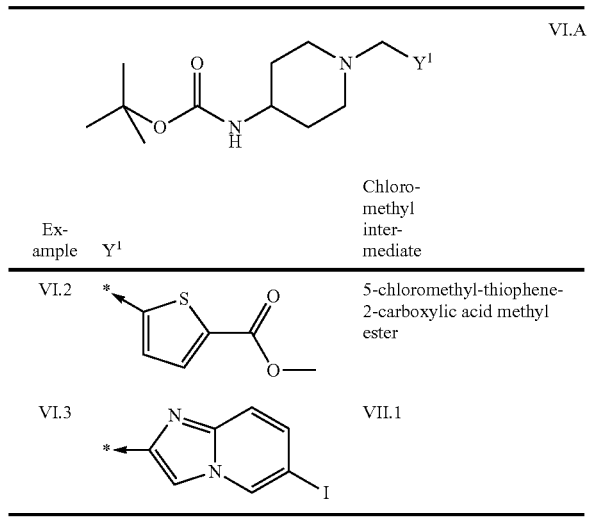

| Example | Y¹ | Chloromethyl intermediate |
|---|---|---|
| VI.2 | 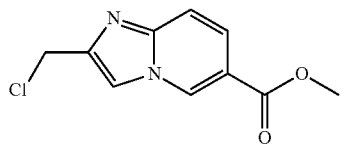 | 5-chloromethyl-thiophene-2-carboxylic acid methyl ester |
| VI.3 | 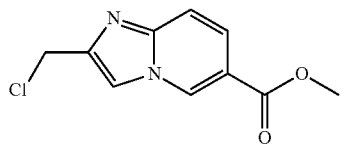 | VII.1 |

Intermediate VII.1

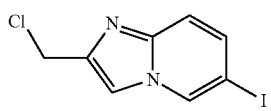

A solution of 1,3-dichloroacetone (6.36 g; 50.11 mmol) and 2-amino-5-iodopyridine (11 g; 50 mmol) in 30 mL dimethoxyethane is stirred at r.t. over night. The precipitate formed is filtered off and washed with dimethoxyethane. To the residue is added 150 mL ethanol and the mixture is refluxed 2 h. The mixture is concentrated, water and NaOH are added and the aqueous layer is extracted twice with DCM/methanol. The organic layer is dried over $MgSO_4$ and the solvent is evaporated.

$C_8H_6ClIN_2$ ESI Mass spectrum: m/z=293 $[M+H]^+$; m/z=337 $[M+HCOO]^-$

Intermediate VIII.1

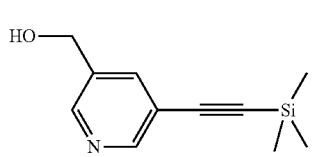

To a solution of (5-bromo-pyridin-3-yl)-methanol (5 g; 26.5 mmol) in 30 mL THF is added triethylamine (11.1 mL; 79.8 mmol) and the flask is flushed with argon. Copper (I) iodide (202 mg; 1.0 mmol), bis-(triphenylphosphin)-palladium-II-chloride (746 mg; 1.0 mmol), triphenylphosphine (279 mg; 1.0 mmol) and trimethylsilylacetylene (4.8 mL; 34.57 mmol) are added and the resulting suspension is stirred 1 h at 80° C. The suspension is concentrated, diluted with DCM and purified by silica gel column chromatography (gradient: DCM/methanol 9:1).

$C_{11}H_{15}NOSi$ ESI Mass spectrum: m/z=206 $[M+H]^+$; m/z=250 $[M+HCOO]^-$

Intermediate IX.1

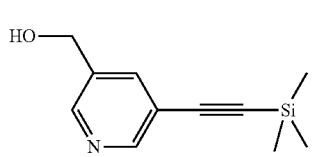

A mixture of methyl-6-aminonicotinate (2.17 g; 14.26 mmol) and 1,3-dichloroacetone (2.0 g; 15.7 mmol) in 20 mL 1,2-dimethoxyethane is refluxed over night. The precipitate formed is filtered off. Water and sodium carbonate are added and the mixture is stirred for a few minutes. The precipitate is filtered off and dried at 50° C.

$C_{10}H_9ClN_2O_2$ ESI Mass spectrum: m/z=225 $[M+H]^+$; m/z=269 $[M+HCOO]^-$

Intermediate X.1

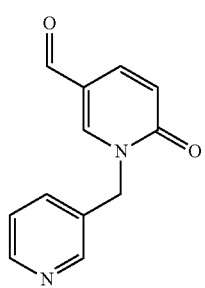

To a solution of 6-hydroxy-pyridine-3-carbaldehyde (500 mg; 4.06 mmol) and 10 mL DMF, cesiumcarbonate (1.40 g; 4.30 mmol) is added and the mixture is stirred 30 minutes at r.t. 3-picolylchloride-hydrochloride (680 mg; 4.15 mmol) is added and the mixture is stirred 2 h at r.t. The mixture is concentrated and purified by silica gel column chromatography (gradient:DCM/methanol 2-4%).

$C_{12}H_{10}N_2O_2$ ESI Mass spectrum: m/z=215 $[M+H]^+$; m/z=213 $[M-H]^-$

Intermediate XI.1

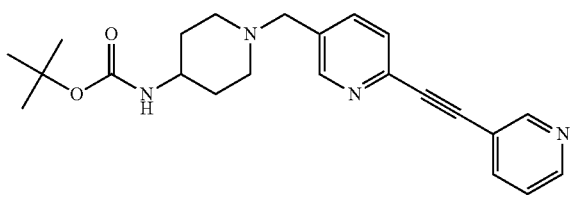

XI.1

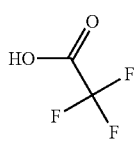

A mixture of 3-ethinylpyridine (66 mg; 0.64 mmol), triethylamine (0.3 mL; 1.9 mmol) and intermediate XII.1 (200 mg; 0.54 mmol) in 5 mL dioxane is flushed with argon. DPPF (155 mg; 0.19 mmol) and copper-(I)-iodide (7 mg; 0.04 mmol) are added and stirred under argon over night at r.t. DCM is added and the mixture is extracted with water. The organic layer is dried with MgSO$_4$, filtered and evaporated. DMF is added to the residue and purified via RP-HPLC (column: sunfire; Water/MeOH; modifier TFA).

$C_{23}H_{28}N_4O_2 * C_2HF_3O_2$ ESI Mass spectrum: m/z=393 $[M+H]^+$; m/z=437 $[M+HCOO]^-$ Intermediate XII.1

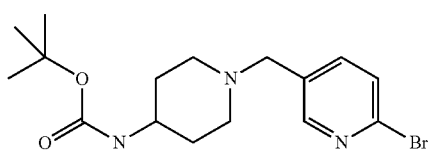

XII.1

A mixture of 6-bromo-pyridine-3-carboxaldehyde (1 g; 5.38 mmol) and Boc-4-aminopiperidine (1.08 g; 5.38 mmol) in 10 mL THF is stirred 30 minutes at RT. The pH is adjusted with acetic acid to pH 5-6 and sodium triacetoxyborohydride (2.28 g; 10.7 mmol) is added slowly. The mixture is stirred 24 h at r.t. Potassium carbonate solution (20%) is added and the mixture is extracted 3 times with ethyl acetate. The organic layer is dried with MgSO$_4$, filtered and evaporated. The residue is purified by silica gel column chromatography (DCM/methanol 9:1). $C_{16}H_{24}BrN_3O_2$ ESI Mass spectrum: m/z=370 $[M+H]^+$; m/z=414$[M+HCOO]^-$ Intermediate XIII.1

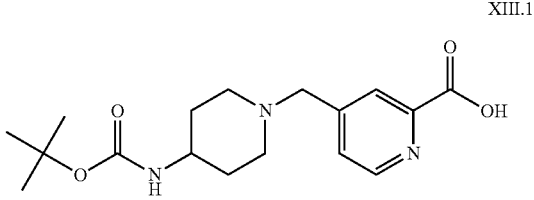 [SMILES: CC(C)(C)OC(=O)NC1CCN(Cc2ccnc(C(=O)O)c2)CC1]

XIII.1

To a solution of intermediate XIV.1 (1 g; 2.86 mmol) in 20 mL, methanol is added sodium hydroxide solution 2 mol/L (4.3 mL; 8.6 mmol) and the mixture is stirred at r.t. over night. The mixture is concentrated, diluted with water, neutralized with 2N HCl and freeze-dried.

$C_{17}H_{25}N_3O_4$
HPLC-MS: RT 0.89 min (HPLC method 1)

Intermediate XIV.1

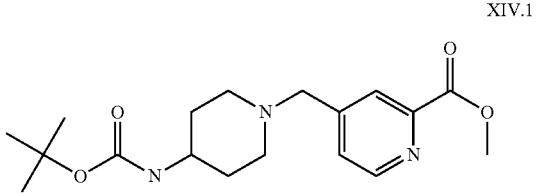 [SMILES: COC(=O)c1cc(CN2CCC(NC(=O)OC(C)(C)C)CC2)ccn1]

XIV.1

To a solution of methyl 4-hydroxymethyl-pyridine-2-carboxylate (3 g; 17.95 mmol) and triethylamine (5.0 mL; 35.89 mmol) in 50 mL DCM is added slowly methanesulfonyl chloride (1.9 mL; 25.1 mmol). The reaction is stirred 1 h at r.t. The mixture is extracted with water, separated and the organic layer is dried with MgSO$_4$, filtered and evaporated. Boc-4-aminopiperidine (3.59 g; 17.95 mmol), triethylamine (5.0 mL; 35.9 mmol) and ACN 50 mL are added and the mixture is stirred 2 h at 85° C. The reaction is cooled to r.t. and the precipitate formed is filtered off and dried in vacuo at 50° C.

$C_{18}H_{27}N_3O_4$ ESI Mass spectrum: m/z=350 $[M+H]^+$; m/z=394$[M+HCOO]^-$

Intermediate XV.1

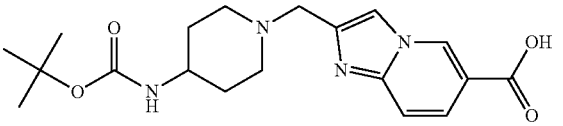

XV.1

To a solution of intermediate VI.1 (2.30 g; 5.92 mmol) in 20 mL methanol, is added 20 mL 1 mol/L sodium hydroxide solution and the mixture is stirred 3 h at r.t. The mixture is neutralized by addition of hydrochloric acid (1 mol/l) and freeze-dried.

$C_{19}H_{26}N_4O_4$ ESI Mass spectrum: m/z=375 [M+H]$^+$; m/z=373 [M−H]$^-$

Intermediate XVI.1

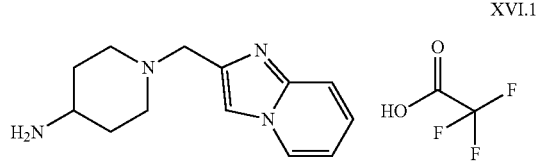

A mixture of intermediate VI.3 (260 mg; 0.57 mmol), Pd/C (50 mg) and 15 mL acetic acid is hydrogenated 3 days at r.t. and 50 PSI. Insolubles are filtered off, the filtrate is concentrated and purified via RP-HPLC (column: sunfire; Water/ACN; modifier TFA). 500 µL TFA and 20 mL DCM are added to the residue. The mixture is stirred 3 h at r.t. and evaporated.

$C_{13}H_{18}N_4 \cdot C_2HF_3O_2$ ESI Mass spectrum: m/z=231 [M+H]$^+$; m/z=275 [M+HCOO]$^-$ Intermediate XVII.1

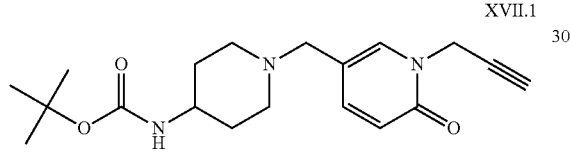

A mixture of 6-oxo-1-prop-2-ynyl-1,6-dihydro-pyridine-3-carbaldehyde (XVIII.1) (1.85 g; 11.48 mmol), BOC-4-aminopiperidine (2.3 g; 11.48 mmol) and 50 mL THF is refluxed 1 h. The pH is adjusted with acetic acid to pH 4-5, sodium triacetoxyborohydride (2.9 g; 13.8 mmol) is added and the mixture is refluxed over night. Water is added and the mixture is extracted with ethyl acetate. Sodium carbonate is added to the water layer until it turns basic and the mixture is extracted 3 times with ethyl acetate. The organic layer is dried with MgSO$_4$, filtered and evaporated.

$C_{19}H_{27}N_3O_3$ ESI Mass spectrum: m/z=346 [M+H]$^+$; m/z=390 [M+HCOO]$^-$

Intermediate XVIII.1

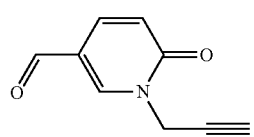

A mixture of 6-hydroxy-pyridine-3-carboxaldehyde (5.0 g; 40.6 mmol), propargyl bromide (5 mL; 44.7 mmol), cesium carbonate (15.9 g; 48.7 mmol) and 200 mL DMF is stirred 3 h at r.t. The mixture is filtered and concentrated. Water and DCM are added to the residue. The mixture is filtered through celite and the layers are separated. The organic layer is dried with MgSO$_4$, filtered and evaporated.

$C_9H_7NO_2$ ESI Mass spectrum: m/z=162 [M+H]$^+$; m/z=160 [M−H]$^-$

Intermediate XIX.1

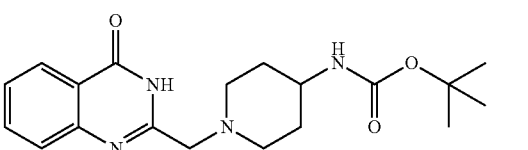

A mixture of 2-chloromethyl-3H-quinazoline-4-one (4 g; 20 mmol), BOC-4-aminopiperidine (4 g; 20 mmol), DIPEA (3.6 g; 30 mmol), 30 mL ACN and 50 mL DMF is stirred 2 h under reflux. 250 mL water is added to the mixture and the precipitate formed is filtered off, washed with water and dried.

$C_{19}H_{26}N_4O_3$ mp: 231° C.

7.2 SYNTHESIS OF EXAMPLES

Example 1.1

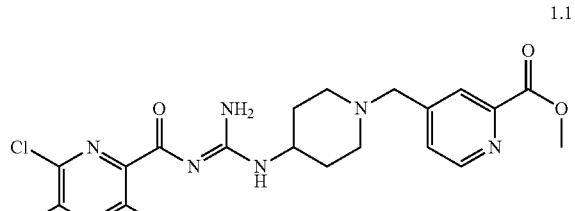

A mixture of 3,5-diamino-6-chloro-N-[(methylsulfanyl)methanimidoyl]pyrazine-2-carboxamide (Intermediate C.1; 1.48 g; 5.66 mmol), the primary amine intermediate I.1 (as a TFA salt; 2.70 g; 5.66 mmol) and TEA (4.92 mL; 35 mmol) in DMF (60 mL) is stirred over night at 80° C. Volatiles are evaporated and the residue is purified by silica gel column chromatography (DCM/(methanol:ammonia 9:1) 100:0→80:20). The product is triturated with ether, filtered off with suction and dried to yield the title compound.

$C_{19}H_{24}ClN_9O_3$ ESI Mass spectrum: m/z=462 [M+H]+

HPLC analytics: RT=0.83 min (HPLC method 1)

The following compounds of general formula 1.A are prepared accordingly using the respective primary amine as indicated. Depending on conditions applied, the procedures may yield a free base, a hydrochloride or dihydrochloride salt, a TFA salt or bis-TFA salt, a zwitterion or other salt forms.

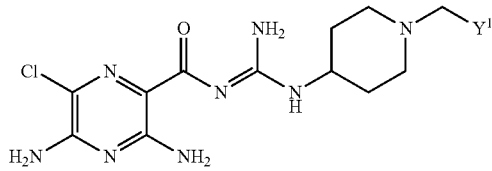

1.A

| Example | Y¹ | Primary amine applied: | Synthesis comment | ESI mass spectrum | HPLC retention time (min) | HPLC method |
|---------|-----|------------------------|-------------------|-------------------|---------------------------|-------------|
| 1.2 | (pyridine with C(O)N(CH₂CH₂OH)₂) | I.2 | Ether decanted from oily product | 535 (M + H)+ | 0.93 | 1 |
| 1.3 | (imidazo[1,2-a]pyridine with C(O)NHCH₂CH₂OCH₂CH₂OH) | I.3 | See footnote a | 574 (M + H)+ | 0.70 | 2 |
| 1.4 | (pyridine-CH₂CH₂-pyridine) | I.4 | See footnotes b, c | 509 (M + H)+ | 0.77 | 3 |
| 1.5 | (2-pyridyl) | e | See footnote b | 404 (M + H)+ | 0.69 | 2 |
| 1.6 | (2-oxo-1-(pyridin-3-ylmethyl)pyridine) | I.5 | See footnote b | 511 (M + H)+ | 0.61 | 4 |
| 1.7 | (imidazo[1,2-a]pyridine-6-carboxylic acid methyl ester) | I.6 | Additional purification: footnote a | 501 (M + H)+ | 0.82 | 4 |
| 1.8 | (imidazo[1,2-a]pyridine-6-C(O)NHCH₂CH₂OH) | I.7 | Additional purification: footnote a | 530 (M + H)+ | 1.04 | 3 |
| 1.9 | (thiazole) | f | See footnote b | 410 (M + H)+ | 0.64 | 2 |
| 1.10 | (4-oxo-3H-quinazolin-2-yl) | I.8 | See footnote b | 471 (M + H)+ | 0.80 | 2 |
| 1.11 | (thiophene-2-carboxylic acid methyl ester) | I.9 | | 467 (M + H)+ | 1.08 | 3 |

-continued

1.A

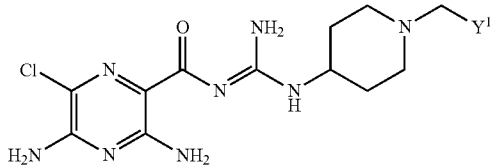

| Example | Y¹ | Primary amine applied: | Synthesis comment | ESI mass spectrum | HPLC retention time (min) | HPLC method |
|---|---|---|---|---|---|---|
| 1.12 | 3-ethynylpyridin-5-yl | I.10 | See footnote d | 428 (M + H)+ | 1.07 | 5 |
| 1.13 | 6-iodoimidazo[1,2-a]pyridin-2-yl | I.11 | See footnote b | 569 (M + H)+ | n.d. | |
| 1.14 | N-(2-(2-hydroxyethoxy)ethyl)picolinamid-4-yl | I.12 | Additional purification: footnote b | 535 (M + H)+ | 0.86 | 1 |
| 1.15 | imidazo[1,2-a]pyridin-2-yl | XVI.1 | See footnote b | 443 (M + H)+ | 0.83 | 6 |
| 1.16 | 1H-benzimidazol-2-yl | g | See footnote b | 443 (M + H)+ | 0.87 | 4 |
| 1.17 | 6-bromopyridin-3-yl | XII.1 | See footnote b | 482 (M + H)+ | 1.23 | 3 |
| 1.18 | 1-(prop-2-yn-1-yl)-2-oxo-pyridin-5-yl | I.14 | | 458 (M + H)+ | 0.98 | 3 | a purification via RP-HPLC (column: Xbridge; water-ACN; modifier NH₃)

b purification via RP-HPLC (column: sunfire; water-ACN; modifier TFA)

c subsequent purification by preparative TLC (silica; DCM/(methanol:ammonia 9:1) 70:30).

d The TMS protected product is further reacted without prior chromatography by stirring in $K_2CO_3$/methanol/water for 2 h to remove the TMS group. The precipitate formed upon addition of ice-water is filtered off and purified by silica gel column chromatography (DCM/(methanol:ammonia 9:1) 100:0 → 90:10).

e Synthesis of the starting material 1-pyridin-2-ylmethyl-piperidin-4-ylamine is described in: WO2006/38001 A1 f Synthesis of the starting material 1-thiazol-4-ylmethyl-piperidin-4-ylamine is described in: Bioorganic and Medicinal Chemistry Letters, 22, 5 (2012) 2052-2062 g The starting material 1-(1H-benzoimidazol-2-ylmethyl)-piperidin-4-ylamine × 3 HCl is prepared from 2-chloromethyl-1H-benzoimidazole and Boc-4-aminopiperidine analogously to the procedure described for the synthesis of intermediate VI.1.

Example 1.19

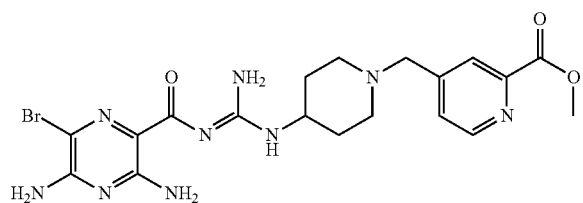 [SMILES: COC(=O)c1cc(CN2CCC(N/C(N)=N/C(=O)c3nc(Br)c(N)nc3N)CC2)ccn1]

The compound is prepared as described for example 1.1 from intermediate C.2 and intermediate I.1. The crude product is purified by RP-HPLC (column: Xbridge; water-ACN; modifier NH₃).

$C_{13}H_{24Br}N_3O_3$ ESI Mass spectrum: m/z=506 [M+H]+
HPLC analytics: RT=0.97 min (HPLC method 7)

Example 2.1

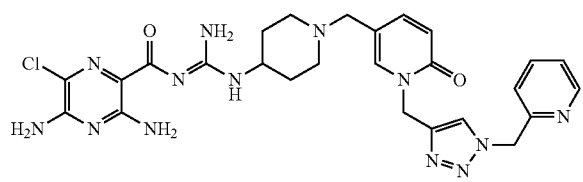 [SMILES: N/C(=N\C(=O)c1nc(Cl)c(N)nc1N)NC1CCN(Cc2ccc(=O)n(Cc3cn(Cc4ccccn4)nn3)c2)CC1]

To a mixture of example 1.18 (400 mg; 0.874 mmol), 2-azidomethyl-pyridine (234 mg; 1.75 mmol) and DMF (5.0 ml) is added a solution of copper(II) acetate (24 mg; 0.131 mmol) and sodium ascorbate (52 mg; 0.242 mmol) in water (0.50 ml). The mixture is stirred at 70° C. over night. Volatiles are evaporated and the residue is purified first by silica gel column chromatography (DCM/(methanol:ammonia 9:1) 100:0→80:20), then by RP-HPLC (column: sunfire; water-ACN; modifier TFA) to yield the title compound.

$C_{26}H_{30}ClN_{13}O_2 \times 2$ TFA ESI Mass spectrum: m/z=592 [M+H]+
HPLC analytics: RT=1.02 min (HPLC method 5)

The following compound (example 2.2) is prepared accordingly using the respective alkyne and azide as indicated. Due to conditions applied, the procedures may yield a free base, a hydrochloride or dihydrochloride salt, a TFA salt or bis-TFA salt, a zwitterion or other salt forms.

Example 2.2

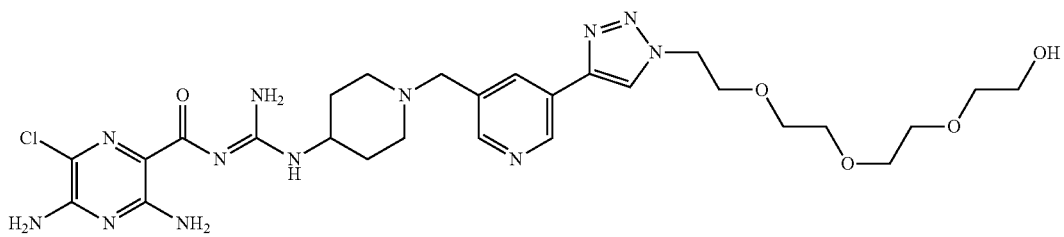 [SMILES: N/C(=N\C(=O)c1nc(Cl)c(N)nc1N)NC1CCN(Cc2cncc(-c3cn(CCOCCOCCOCCO)nn3)c2)CC1]

Alkyne applied: example 1.12; Azide applied: 1-azido-3,6,9-trioxaundecane-11-ol $C_{27}H_{39}ClN_{12}O_5$ ESI Mass spectrum: m/z=647 [M+H]+
HPLC analytics: RT=1.00 min (HPLC method 5)

Example 3.1

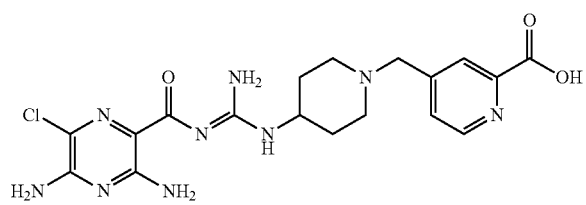 [SMILES: N/C(=N\C(=O)c1nc(Cl)c(N)nc1N)NC1CCN(Cc2ccnc(C(=O)O)c2)CC1]

A mixture of the ester compound example 1.1 (150 mg; 0.325 mmol), lithium hydroxide (1M in water; 0.649 ml; 0.649 mmol) and THF (2.0 ml) is stirred at r.t. for 7 days. Volatiles are evaporated and the residue is purified by RP-HPLC (column: C18; water-ACN; modifier TFA) to yield the title compound.

$C_{18}H_{22}ClN_9O_3 \times 2$ TFA ESI Mass spectrum: m/z=448 [M+H]+
HPLC analytics: RT=0.74 min (HPLC method 3)

The following compound (example 3.2) is prepared accordingly using the respective ester compound as indicated. Due to conditions applied, the procedures may yield a free base, a hydrochloride or dihydrochloride salt, a TFA salt or bis-TFA salt, a zwitterion or other salt forms.

Example 3.2

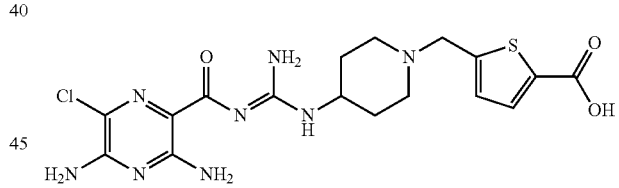

Ester applied: example 1.11
$C_{17}H_{21}ClN_8O_3S$ ESI Mass spectrum: m/z=453 [M+H]+
HPLC analytics: RT=0.94 min (HPLC method 3)

Example 4.1

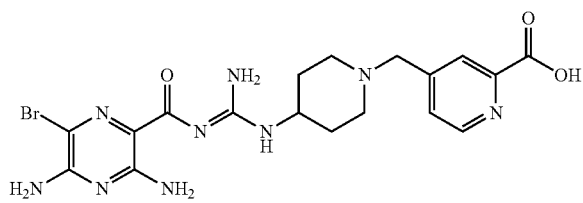 [SMILES: N/C(=N\C(=O)c1nc(Br)c(N)nc1N)NC1CCN(Cc2ccnc(C(=O)O)c2)CC1]

A mixture of example 1.19 (200 mg; 0.288 mmol), aqueous ammonia (32%; 0.20 ml) and DMF is stirred over night at r.t. Sodium hydroxide (4 mol/l; 0.20 ml) is added and the mixture is again stirred over night, then acidified by addition of hydrochloric acid (4 mol/l). Water (2 ml) is added and the precipitate is filtered off and dried in vacuo at 50° C. to yield the title compound.

$C_{18}H_{22}BrN_9O_3 \times 3HCl$ ESI Mass spectrum: m/z=492 [M+H]+

HPLC analytics: RT=0.45 min (HPLC method 8)

8. ANALYTICAL METHODS AND PREPARATIVE CHROMATOGRAPHY

As a rule, $^1$H-NMR and mass spectra have been obtained for the compounds prepared. Mass peaks given (e.g. (M+H)$^+$, (M+HCOO)—) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. For silica gel chromatographic purifications, silica gel from Millipore (MATREX™, 35-70 my) is used.

Preparative Thin Layer Chromatochraphy (TLC):

Preparative TLC plates from Merck (PLC Silica gel 60 $F_{254+366}$, 2 mm) are used. Product containing bands are scraped off and the resulting product-on-silica powder is extracted with DCM, methanol or a mixture thereof (depending on product solubility). Silica is filtered off and the filtrate is evaporated to dryness to yield the purified compound.

Preparative HPLC:

Stationary phase: XBridge C18; 10 μm or Sunfire C18; 10 μm (both from waters, www.waters.com)

Analytical HPLC/MS Methods

The HPLC retention times given are measured under the following parameters.

HPLC Method 1

| Column: XBridge C18, 4.6 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4.5 | 60 |
| 2.40 | 0 | 100 | 4.5 | 60 |

HPLC Method 2

| Column: XBridge C18, 3 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.65 | 0 | 100 | 2.9 | 60 |

HPLC Method 3

| Column XBridge C18, 4.6 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

HPLC Method 4

| Column Sunfire C18, 3 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

HPLC Method 5

| Column Sunfire C18, 4.6 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

HPLC Method 6

| Column: Sunfire C18, 4.6 × 30 mm, 2.5 μm (Waters) | | | | |
|---|---|---|---|---|
| Gradient time [min] | % Sol [H2O, 0.1% TFA] | % Sol [Methanol, 0.1% TFA] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4 | 60 |
| 2.35 | 0 | 100 | 4 | 60 |

HPLC Method 7

| Säule: XBridge C18, 4.6 × 30 mm, 3.5 µm (Waters) | | | | |
|---|---|---|---|---|
| Gradient time [min] | % Sol [H2O, 0.1% NH3] | % Sol [ACN] | Flow [ml/min] | Temp [° C.] |
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

HPLC Method 8

| Column: Sunfire, 3 × 30 mm, 2.5 µm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

The following abbreviations are used above and hereinafter:
ACN Acetonitrile
BOC tert-Butoxycarbonyl
DCM Methylene chloride
DIPEA Diisopropyl-ethylamine
DMF N,N-Dimethylformamide
DPPF 1,1'-Bis(diphenylphosphino)ferrocene
ESI Electrospray ionization
h hour
HATU O-(7-Azabenzotriazol-1-yl)-N,N,N',N'-tetramethyluronium hexafluorophosphate
MeOH methanol
Min minutes
Mp melting point
n.d. not determined
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluronium-tetrafluoroborate
TEA Triethylamine
TFA Trifluoroacetic acid
THF Tetrahydrofuran
TMS Trimethylsilyl

arrow and asterisk indicate the binding site, i.e. the point of attachment (here: atom "A") within a chemical entity (here exemplified by the group "A-R")

9. PHARMACOLOGICAL TEST METHOD

Ussing Chamber:

Mouse kidney M-1 cells were cultivated in DMEM containing 5% FCS and 5 µM dexamethasone for 10 to 12 days on polyester transwell filters. Filters were inserted into a teflon-coated well-plate which fit into the in-house ussing chamber system. Prior to measurement the medium of M-1 cells was replaced with Caco-2 transport buffer (Invitrogen, Germany). During measurements, the Ussing chamber temperature was kept at 37° C. Short circuit currents ($I\_sc$) were measured in the voltage-clamp mode using an in-house built amplifier (Boehringer Ingelheim, Biberach) with the software package Lab View for data acquisition and analysis. The transepithelial electrical resistance (TEER) was determined by the application of voltage steps of ±5 mV every 5 sec. Compounds were administered at a final concentration of 3 µM or at increasing concentrations (1-3-10 µM) to the apical solution. At the end of each experiment the amiloride sensitive $I\_SC$ was measured by adding 3 µM amiloride to the apical compartment. Results are expressed as inhibition in percent of the amiloride effect or as $IC_{50}$. With the example compounds given above, the following $IC_{50}$ values were determined in the Ussing Chamber assay:

| Example | 1.1 | 1.2 | 1.3 | 1.4 | 1.5 | 1.6 | 1.7 | 1.8 | 1.9 | 1.10 | 1.11 | 1.12 |
|---|---|---|---|---|---|---|---|---|---|---|---|---|
| $IC_{50}$ [nM] | 3 | 10 | 18 | 3 | 15 | 9 | 4 | 11 | 17 | 4 | 3 | 4 |
| Example | 1.13 | 1.14 | 1.15 | 1.16 | 1.17 | 1.18 | 1.19 | 2.1 | 2.2 | 3.1 | 3.2 | 4.1 |
| $IC_{50}$ [nM] | 3 | 4 | 6 | 5 | 5 | n.d. | 4 | 6 | 12 | 21 | 31 | 16 |

10. INDICATIONS

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. COMBINATIONS

The compounds of formula (I) may be used on their own or in conjunction with other active substances of (I) according to the invention. If desired the compounds of formula (I) may also be used in combination with other pharmaceutically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

12. FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilizers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavorings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmaceutically acceptable substance which is not an active substance but which can be formulated with the active substance or substances in the pharmaceutically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavourings, vitamins and/or other additives known in the art. The additives also include pharmaceutically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

Capsule for Powder Inhalation 1 capsule contains:

| active substance | 0.5 mg |
|---|---|
| lactose for inhalation | 5.0 mg |
| | 5.5 mg |

Preparation:

The active substance is mixed with lactose for inhalation. The mixture is packed into capsules in a capsule-making machine (weight of the empty capsule approx. 50 mg).

| weight of capsule: | 55.5 mg |
|---|---|
| size of capsule = | 3 |

The invention claimed is:
1. A compound of formula (I),

$$(I)$$

wherein
$R^1$ denotes H or methyl,
$R^2$ is selected from a group consisting of
   H, $C_{1-4}$-alkyl-, $C_{1-4}$-alkyl-O—CO—, $C_{1-4}$-alkyl-O—CO—$C_{1-4}$-alkyl-, $C_{1-4}$-alkyl-O—$C_{1-4}$-alkyl-, HO—CO— and HO—CO—$C_{1-4}$-alkyl-,
$R^3$ denotes H or methyl,
$R^4$ denotes H or methyl, or
$R^3$ and $R^4$ together form an ethylene bridge
m, n independently from each other with the proviso that (m+n)<4, denote 0, 1 or 2,
X denotes halogen,
$L^1$ denotes a bond or is selected from a group consisting of —$CH_2$—, —$CH_2$—$CH_2$—, —$CH_2O$—, —CO—, —S—, —SO—, —$SO_2$—, —S—$CH_2$—, SO—$CH_2$— and —$SO_2$—$CH_2$—
$Y^1$ denotes a C-linked five- or six-membered heteroaromatic moiety or a C-linked 8-10-membered heteroaromatic moiety, optionally substituted by $R^5$, $R^6$, $R^7$, and $R^8$, wherein
$R^7$ and $R^8$ independently from each other are selected from a group consisting of
   H, halogen, CN, $C_{1-4}$-alkyl-optionally substituted by one or more F atoms, HC≡C—, OH, $C_{1-4}$-alkyl-O— and HO—$CH_2$—,
$R^5$ is selected from a group consisting of
   H, halogen, =O, CN, $N_3$, $C_{1-4}$-alkyl-optionally substituted by one or more F atoms, HC≡C—, OH, $C_{1-4}$-alkyl-O—, HO—$CH_2$—, $H_2C$=CH—$CH_2$—O—, HC≡C—$CH_2$—, HC≡C—$CH_2$—O—, —$NR^{5.1}R^{5.2}$, $H_2N$—C(NH)—, $H_2N$—C(NH)NH—, $H_2N$—C(NH)NH—$CH_2$—, —COOH, $C_{1-4}$-alkyl-OCO—, —$C_{1-4}$-alkyl-COOH, —$C_{1-4}$-alkyl-COO—$C_{1-4}$-alkyl, —$OCH_2$—COOH, $OCH_2$—COO—$C_{1-4}$-alkyl-, and —$B(OH)_2$,
wherein,
$R^{5.1}$ denotes H, $C_{1-4}$-alkyl-, $C_{1-4}$-alkyl-CO— or $C_{1-4}$-alkyl-$SO_2$—,
$R^{5.2}$ denotes H or $C_{1-4}$-alkyl-,
or
$R^{5.1}$ and $R^{5.2}$ together with the nitrogen atom they are attached to form an optionally substituted 4-7-membered heterocycle containing at least one N-atom,
$R^6$ is selected from a group consisting of
   H, halogen, =O, CN, $N_3$, $C_{1-4}$-alkyl-optionally substituted by one or more F atoms, HC≡C—, OH, $C_{1-4}$-alkyl-O—, HO—$CH_2$—, $H_2C$=CH—$CH_2$—O—, HC≡C—$CH_2$—, HC≡C—$CH_2$—O—, —$NR^{6.1}R^{6.2}$, $H_2N-C(NH)-$, $H_2N-C(NH)NH-$, $H_2N-C(NH)NH-CH_2-$, $-COOH$, $C_{1-4}$-alkyl-OCO—,
$-C_{1-4}$-alkyl-COOH, $-C_{1-4}$-alkyl-COO—$C_{1-4}$-alkyl, $-OCH_2-COOH$, $-OCH_2-COO-C_{1-4}$-alkyl, and $-B(OH)_2$,
wherein,
$R^{6.1}$ denotes H, $C_{1-4}$-alkyl-, $C_{1-4}$-alkyl-CO— or $C_{1-4}$-alkyl-SO$_2$—,
$R^{6.2}$ denotes H or $C_{1-4}$-alkyl-,
or
$R^{6.1}$ and $R^{6.2}$ together with the nitrogen atom they are attached to form an optionally substituted 4-7-membered heterocycle containing at least one N-atom,
or
$R^6$ denotes -$L^2$-$Y^2$-$L^3$-$R^{6.5}$
wherein,
$L^2$ denotes a bond or is selected from a group consisting of —CH$_2$—, —CH$_2$—CH$_2$—, and —CH$_2$—CO—,
or, with the proviso that $L^2$ is attached to a carbon atom of $Y^1$, and is selected from a group consisting of —O—, —CH$_2$—O—, —O—CH$_2$—, —CO—, —CO—CH$_2$—, —S—, —SO—, —SO$_2$— and —O—CO—,
$Y^2$ denotes a bond or
is selected from a group consisting of
$Y^{2.1}$, —CO—, —NR$^{11}$—CO—, —CO—NR$^{11}$—, —$Y^{2.1}$—CONR$^{11}$—, —$Y^{2.1}$—CO— and —NR$^{11}$—CO—$Y^{2.1}$—,
with the proviso that carbonyl moieties are not directly attached to nitrogen atoms of unsaturated heterocycles and are not directly attached to another carbonyl moiety,
wherein
$R^{11}$ denotes -$L^4$-$R^9$,
$Y^{2.1}$ denotes a cyclic linker selected from either a phenylene group optionally substituted by -$L^5R^{10}$, or an optionally substituted heteroaromatic or heterocyclic moiety each containing at least one nitrogen atom,
$L^3$, $L^4$, $L^5$ independently from each other denote a bond or a linear chain of formula (m)

—(CH$_2$)$_i$—[O—(CH$_2$)$_{g1}$]$_{p1}$—[O—(CH$_2$)$_{g2}$]$_{p2}$— (m)

wherein
i denotes 0, 1, 2 or 3,
g1, g2 independently from each other denote 2 or 3,
p1, p2 independently from each other denote 0, 1, 2 or 3,
with the provisio that the linear chain is consisting of 1 to 12 moieties selected from a group consisting of —CH$_2$—, and —O—,
$R^{6.5}$, $R^9$, $R^{10}$ independently from each other are selected from a group consisting of
H, halogen, CN, $C_{1-4}$-alkyl, HC≡C—, OH, $C_{1-4}$-alkyl-O—, HO—CH$_2$—, H$_2$C═CH—CH$_2$—O—, HC≡C—CH$_2$—O—, B(OH)$_2$, BF$_3^-$, —S(O)$_2$OH, —C(CH$_2$OH)$_3$, —CH(CH$_2$OH)$_2$, and —CH(OH)CH$_2$OH,
or
independently from each other denote a five- or six membered heteroaromatic or heterocyclic moiety, optionally substituted by one or two substituents independently selected from
halogen, CN, $C_{1-4}$-alkyl-(optionally substituted by one or more F atoms), HC≡C—, OH, $C_{1-4}$-alkyl-O—, HO—CH$_2$—, and tautomers and optionally the pharmaceutically acceptable acid addition salts thereof.

2. A compound of formula (I) according to claim 1, wherein m, n independently from each other with the proviso that 0<(m+n)<4, denote 0, 1 or 2, X denotes Cl or Br, and $L^1$ denotes a bond or is selected from a group consisting of —CH$_2$— and —CH$_2$—CH$_2$—, $Y^1$ is selected from a group consisting of a linker of formula (a1) to (k1)

(a1)

(b1)

(c1)

(d1)

(e1)

(f1)

(g1)

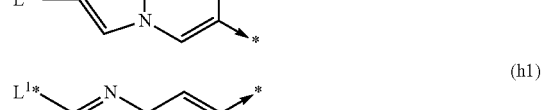
(h1)

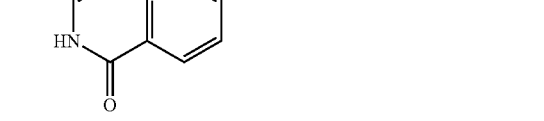
(i1)

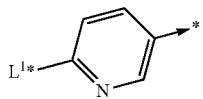
(k1)

*denotes the attachment point to a substituent of $Y^1$, and $L^1$* denotes the attachment point to $L^1$.

3. A compound of formula (I) according to claim 1, wherein $R^1$, $R^2$, $R^3$ and $R^4$ denote hydrogen, m, n denote 1, and $L^1$ denotes a bond.

4. A compound of formula (I) according to claim 1, wherein $R^5$ denotes hydrogen or is selected from a group consisting of halogen, =O and methyl, $R^6$ denotes hydrogen or is selected from a group consisting of $C_{1-4}$-alkyl-OCO—, HC≡C—, halogen, HC≡C—$CH_2$— and —COOH, or $R^6$ denotes -$L^2$-$Y^2$-$L^3$-$R^{6.5}$ wherein, $L^2$ denotes a bond or is selected from a group consisting of —$CH_2$— and —$CH_2$—$CH_2$—, $Y^2$ denotes a bond or is selected from a group consisting of $Y^{2.1}$, —CO— and —CO—$NR^{11}$—, with the proviso that carbonyl moieties are not directly attached to nitrogen atoms of unsaturated heterocycles and are not directly attached to another carbonyl moiety, wherein $R^{11}$ denotes -$L^4$-$R^9$, and $Y^{2.1}$ denotes a pyridyl or triazolyl moiety, $L^3$, $L^4$ independently from each other denote a bond or a linear chain of formula (m)

—$(CH_2)_i$—[O—$(CH_2)_{g1}$]$_{p1}$—[O—$(CH_2)_{g2}$]$_{p2}$— (m)

wherein i denotes 0, 1, 2 or 3 g1, g2 independently from each other denote 2, and p1, p2 independently from each other denote 0, 1 or 2, $R^{6.5}$, $R^9$ independently from each other denote H or OH, or $R^{6.5}$ denotes pyridyl, and $R^7$, $R^8$ denote hydrogen.

5. A compound of formula (I) according to claim 1, wherein $R^1$ denotes H, $R^2$ denotes H, X denotes Cl or Br, $L^1$ denotes a bond or is selected from a group consisting of —$CH_2$—, —$CH_2$—$CH_2$—, —$CH_2O$—, and —CO—, $Y^1$ denotes a moiety selected from a group consisting of a linker of formula (a1) to (z1)

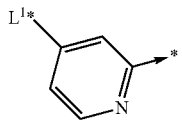
(a1)

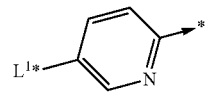
(b1)

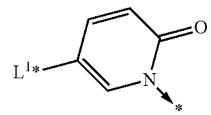
(c1)

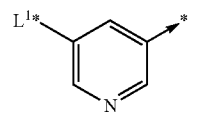
(d1)

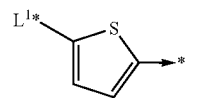
(e1)

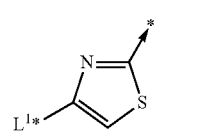
(f1)

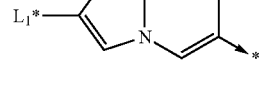
(g1)

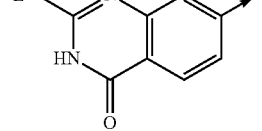
(h1)

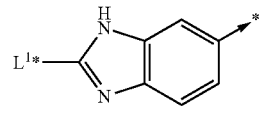
(i1)

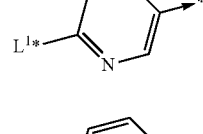
(k1)

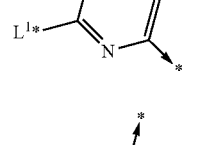
(l1)

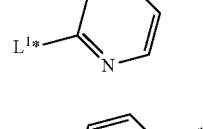
(m1)

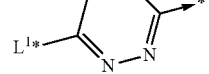
(n1)

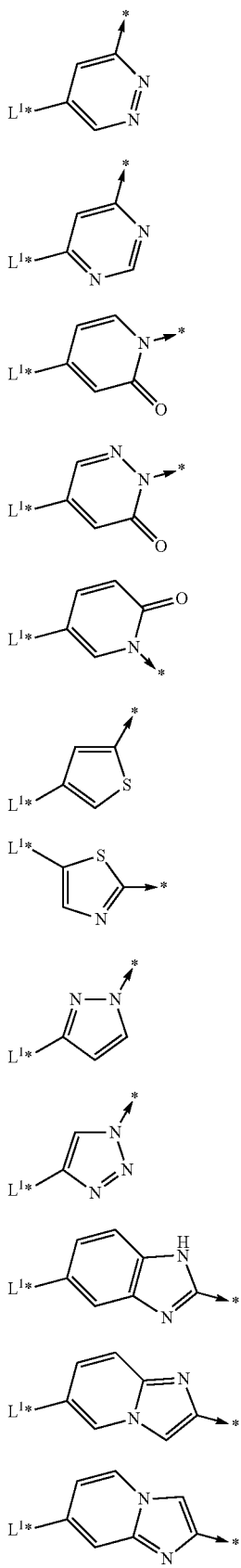
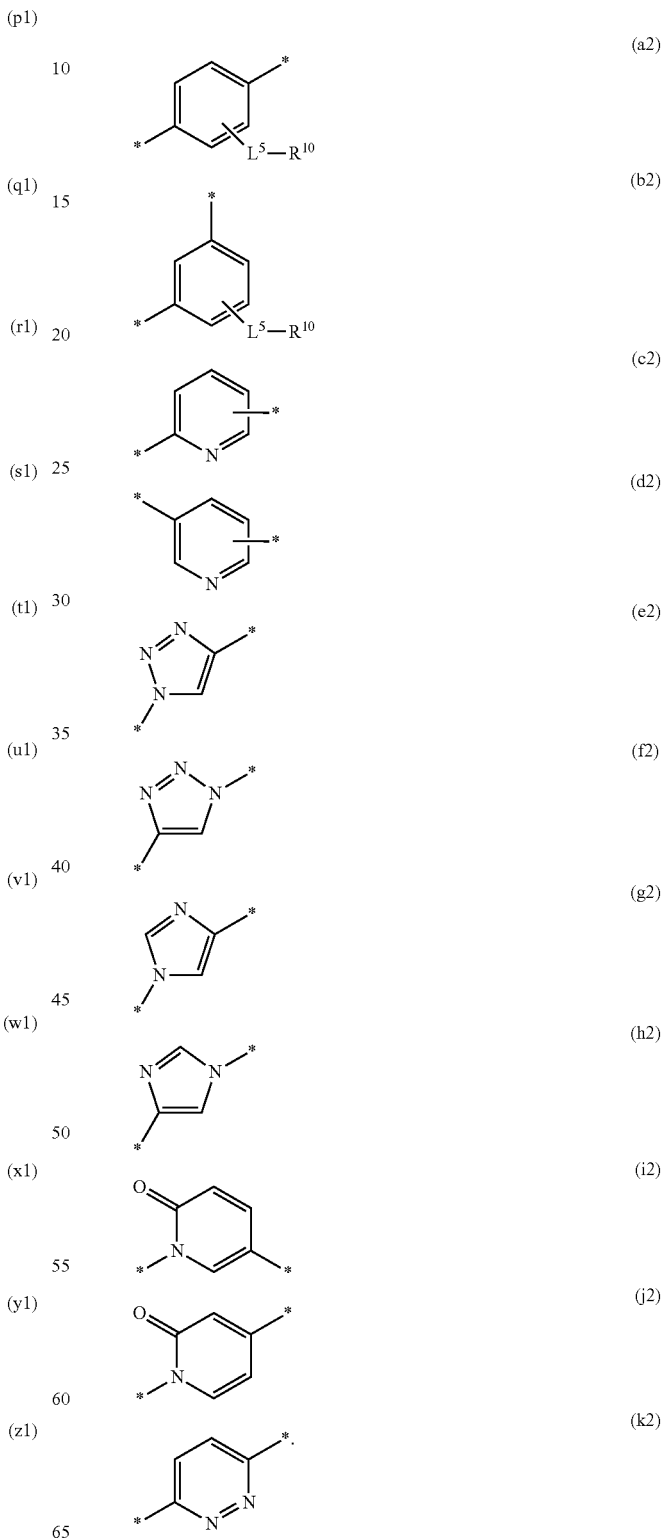
↗: denotes the attachment point to a substituent of Y¹
L¹* denotes the attachment point to L¹
each optionally substituted by R⁵ or R⁶, and
$Y^{2.1}$ is selected from a group consisting of a linker of formula (a2) to (k2)

6. A compound of formula (I) according to claim 1, wherein
$R^3$, $R^4$ denote H,
m, n independently from each other with the proviso that 0<(m+n)<4, denote 0, 1 or 2,
X denotes Cl or Br,
$L^1$ denotes a bond or is selected from a group consisting of —$CH_2$—, and —$CH_2$—$CH_2$—, and
$R^{6.5}$, $R^9$, $R^{10}$ independently from each other are selected from a group consisting of
H, HC≡C—, OH and 2-pyridyl.

7. A compound of formula (I) according to claim 1, wherein
$R^5$ is selected from a group consisting of
H, halogen and $C_{1-4}$-alkyl-, optionally substituted by one or more F atoms,
and
$R^6$ denotes —COOH,
$Y^1$ is selected from among

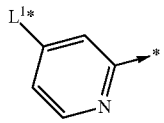 (a1)

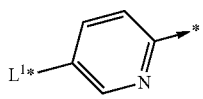 (b1)

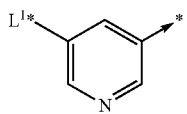 (d1)

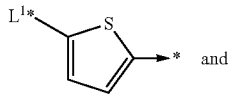 and (e1)

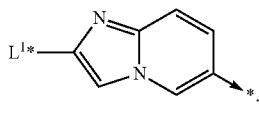 (g1)

8. A compound of formula (I) according to claim 1, wherein
$R^5$ is selected from a group consisting of
H, halogen, and $C_{1-4}$-alkyl-optionally substituted by one or more F atoms,
$R^6$ denotes
$C_{1-4}$-alkyl-OCO—,
$Y^1$ is selected from among

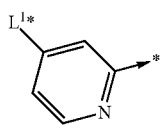 (a1)

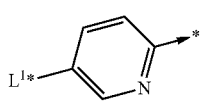 (b1)

-continued

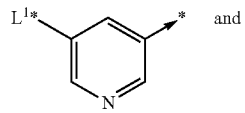 and (d1)

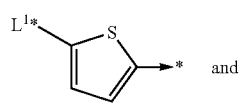 and (e1)

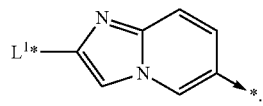 (g1)

9. A compound of formula (I) according to claim 1, wherein
$R^6$ denotes -$L^2$-$Y^2$-$L^3$-$R^{6.5}$
wherein,
$L^2$ denotes a bond or is selected from a group consisting of —$CH_2$—, and —$CH_2$—$CH_2$—,
or, with the proviso that $L^2$ is attached to a carbon atom of $Y^1$, is selected from a group consisting of —O—, —$CH_2$—O—, and —O—$CH_2$—,
$Y^2$ denotes —CO—$NR^{11}$— or —$Y^{2.1}$—$CONR^{11}$—,
with the proviso that carbonyl moieties are not directly attached to nitrogen atoms of unsaturated heterocycles and are not directly attached to another carbonyl moiety,
$L^3$, $L^4$, $L^5$ independently from each other denote a bond or a linear chain of formula (m)

—$(CH_2)_l$—[O—$(CH_2)_{g1}$]$_{p1}$—[O—$(CH_2)_{g2}$]$_{p2}$— (m)

wherein
l denotes 0, 1, 2 or 3,
g1, g2 independently from each other denote 2 or 3,
p1, p2 independently from each other denote 0, 1, 2 or 3,
with the provisio that the linear chain is consisting of 1 to 12 moieties selected from a group consisting of —$CH_2$—, and —O—,
and with the proviso that p1+p2<4.

10. A compound of formula (I) according to claim 1, wherein
$R^6$ denotes -$L^2$-$Y^2$-$L^3$-$R^{6.5}$
wherein,
at least one out of $L^3$, $L^4$, and $L^5$ denotes a linear chain of formula (m)

—$(CH_2)_l$—[O—$(CH_2)_{g1}$]$_{p1}$—[O—$(CH_2)_{g2}$]$_{p2}$— (m)

wherein
i denotes 0, 1, 2 or 3,
g1, g2 independently from each other denote 2 or 3,
p1, p2 independently from each other denote 0, 1, 2 or 3,
with the provisio that the linear chain is consisting of 6 to 12 moieties selected from a group consisting of —$CH_2$—, and —O—,
and with the proviso that p1+p2>1.

11. A pharmaceutical composition comprising at least one compound according to claim 1 or a pharmaceutically acceptable salt thereof and a pharmaceutically acceptable carrier.

12. A medicament combination which contains, besides one or more compounds according to claim 1, as further active substances, one or more compounds selected from among the categories of ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators.

* * * * *